United States Patent
Middlesworth

(10) Patent No.: US 11,034,072 B2
(45) Date of Patent: Jun. 15, 2021

(54) PRESTRETCHED ELASTIC FILM IN PERSONAL HYGIENE PRODUCTS

(71) Applicant: Berry Global, Inc., Evansville, IN (US)

(72) Inventor: Jeffrey A. Middlesworth, Wauconda, IL (US)

(73) Assignee: Berry Global, Inc., Evansville, IN (US)

(*) Notice: Subject to any disclaimer, the term of this patent is extended or adjusted under 35 U.S.C. 154(b) by 283 days.

(21) Appl. No.: 15/806,403

(22) Filed: Nov. 8, 2017

(65) Prior Publication Data

US 2018/0126619 A1 May 10, 2018

Related U.S. Application Data

(60) Provisional application No. 62/419,805, filed on Nov. 9, 2016, provisional application No. 62/455,827, filed on Feb. 7, 2017.

(51) Int. Cl.
*B29C 48/00* (2019.01)
*B29C 48/18* (2019.01)
(Continued)

(52) U.S. Cl.
CPC .... *B29C 48/0018* (2019.02); *A61F 13/15707* (2013.01); *A61F 13/49012* (2013.01); *B29C 39/123* (2013.01); *B29C 39/42* (2013.01); *B29C 41/26* (2013.01); *B29C 41/42* (2013.01); *B29C 48/022* (2019.02); *B29C 48/18* (2019.02); *B29C 48/21* (2019.02); *B29C 48/914* (2019.02); *B29C 48/916* (2019.02); *B29C 48/917* (2019.02); *B29C 55/02* (2013.01); *A61F 2013/15715* (2013.01); *B29C 55/06* (2013.01); *B29C 55/065* (2013.01); *B29K 2023/0625* (2013.01); *B29K 2023/0633* (2013.01); *B29K 2023/12* (2013.01); *B29K 2105/04* (2013.01); *B29K 2995/0046* (2013.01); *B29K 2995/0065* (2013.01); *B29L 2007/008* (2013.01); *B29L 2009/00* (2013.01); *B29L 2031/4878* (2013.01)

(58) Field of Classification Search
CPC ......................... B29C 48/0018; B29C 48/917
See application file for complete search history.

(56) References Cited

U.S. PATENT DOCUMENTS 3,213,172 A   10/1965   Hoelzer
4,501,712 A   2/1985    Heyer
(Continued)

FOREIGN PATENT DOCUMENTS

CN   1201382 A   12/1998
CN   1414843 A   4/2003
(Continued)

OTHER PUBLICATIONS

International (PCT) Search Report and Written Opinion for PCT/US17/60574 dated Dec. 27, 2017, BP-511 PCT II, 12 pages.
(Continued)

*Primary Examiner* — Jacob T Minskey
*Assistant Examiner* — Virak Nguon
(74) *Attorney, Agent, or Firm* — Barnes & Thornburg LLP

(57) ABSTRACT

Stretched elastic films include a polyolefin, a styrene block copolymer, a non-styrene block copolymer, or a combination thereof. Methods for forming polymeric films and articles of manufacture prepared therefrom are described.

22 Claims, 5 Drawing Sheets

(51) Int. Cl.

| | |
|---|---|
| *B29C 48/21* | (2019.01) |
| *B29C 48/88* | (2019.01) |
| *B29C 41/26* | (2006.01) |
| *B29C 41/42* | (2006.01) |
| *A61F 13/15* | (2006.01) |
| *A61F 13/49* | (2006.01) |
| *B29C 39/12* | (2006.01) |
| *B29C 39/42* | (2006.01) |
| *B29C 55/02* | (2006.01) |
| *B29C 55/06* | (2006.01) |
| *B29K 23/00* | (2006.01) |
| *B29K 105/04* | (2006.01) |
| *B29L 7/00* | (2006.01) |
| *B29L 9/00* | (2006.01) |
| *B29L 31/48* | (2006.01) |

(56) References Cited

U.S. PATENT DOCUMENTS

| | | |
|---|---|---|
| 4,925,520 A | 5/1990 | Beaudoin |
| 5,000,806 A | 3/1991 | Merkatoris |
| 5,296,080 A | 3/1994 | Merkatoris |
| 5,916,692 A | 6/1999 | Brambilla |
| 6,482,278 B1 | 11/2002 | McCabe |
| 8,172,977 B2 | 5/2012 | McCabe |
| 8,460,495 B2 | 6/2013 | McCabe |
| 8,673,098 B2* | 3/2014 | McCabe ............ A61F 13/15593 156/163 |
| 9,193,136 B2* | 11/2015 | Iodice .................... B32B 7/02 |
| 2002/0081423 A1* | 6/2002 | Heffelfinger ........... B32B 27/04 428/297.4 |
| 2004/0005835 A1 | 1/2004 | Zhou |
| 2005/0043460 A1* | 2/2005 | McCormack ........... B32B 37/12 524/425 |
| 2005/0214506 A1 | 9/2005 | Lee et al. |
| 2008/0177242 A1 | 7/2008 | Chang |
| 2008/0226920 A1 | 9/2008 | Parkinson |
| 2009/0258210 A1* | 10/2009 | Iyad ...................... C08L 23/142 428/220 |
| 2012/0273129 A1 | 11/2012 | Handziak |
| 2013/0126070 A1* | 5/2013 | Siqueira .............. A61F 13/4902 156/160 |
| 2013/0153577 A1 | 6/2013 | Su |
| 2014/0349195 A1* | 11/2014 | Ogawa ...................... C08J 5/18 429/254 |
| 2015/0164700 A1 | 6/2015 | Schwartz |
| 2016/0325005 A1* | 11/2016 | Wang ..................... A61L 15/18 |
| 2017/0253012 A1* | 9/2017 | Chang .................... B32B 5/022 |
| 2017/0305061 A1 | 10/2017 | Topolkaraev |
| 2018/0223092 A1* | 8/2018 | Degroot .................. B32B 5/022 |
| 2019/0270877 A1* | 9/2019 | Barnes ............... B29D 99/0064 |

FOREIGN PATENT DOCUMENTS

| | | |
|---|---|---|
| CN | 101137494 | 3/2008 |
| CN | 102602087 B | 2/2016 |
| WO | 2015153993 | 10/2015 |
| WO | 2015187447 | 12/2015 |

OTHER PUBLICATIONS

International PCT Search Report and Written Opinion for PCT App. No. PCT/US17/60560 dated Mar. 5, 2018, 10 pages.

Kapur. et at. "Aging of quenched polypropylene." Journal of Polymer Science: Part B: Polymer Physics [online], Nov. 1972 [Retrieved on Jan. 28, 2017], vol. 10. Issue 11. pp. 2107-2124, 18 pages.

Taiwan Office Action for Taiwan App. No. 10618691 completed May 11, 2018, BP-511 TW II, 20 pages, with brief English translation included.

Taiwan Office Action for Taiwan App. No. 106138690, BP-510 TW II, 17 pages, brief English translation provided.

Office Action dated Nov. 7, 2019 for U.S. Appl. No. 15/806,402, BP-510 US-U II,(pp. 1-15).

* cited by examiner

PRESTRETCHED ELASTIC FILM IN PERSONAL HYGIENE PRODUCTS

PRIORITY CLAIM

This application claims priority under 35 U.S.C. § 119(e) to U.S. Provisional Application Ser. No. 62/419,805, filed Nov. 9, 2016, and U.S. Provisional Application Ser. No. 62/455,827, filed Feb. 7, 2017, each of which is expressly incorporated by reference herein.

BACKGROUND

The present disclosure relates to polymeric materials, and particularly to polymeric films. More particularly, the present disclosure relates to elastic films formed from polymeric material.

SUMMARY

According to the present disclosure, an elastic film is made using a manufacturing process. The manufacturing process comprises the steps of extruding a composition to form a molten web and casting the molten web to form a quenched film.

In illustrative embodiments, the manufacturing process used to form the elastic film further includes stretching the quenched film to form a stretched film. Optionally, the manufacturing process may further include the step of relaxing the stretched film to form a relaxed film, and/or the step of ageing the quenched film to form an aged film.

In illustrative embodiments, the composition extruded to form the molten web comprises a polyolefin, a styrene block copolymer, a non-styrene block copolymer, or a combination thereof. The quenched film is formed by casting the molten web against a surface of a chill roll using a vacuum box and/or blowing air (e.g., an air knife and/or an air blanket). The quenched film is stretched in a machine direction in at least a 2:1 draw to form the stretched film.

In illustrative embodiments, a stretched elastic film comprises a multi-layer structure comprising at least one first film layer interposed between at least one second film layer and at least one third film layer.

In illustrative embodiments, a stretched elastic film comprises an elastomer, and the stretched elastic film, after relaxation, has a load at 100% of less than about 300 grams/inch.

In illustrative embodiments, a process for making a multi-layer article comprises attaching at least a portion of a stretched elastic film to at least a portion of a non-woven layer via ultrasonic bonding.

In illustrative embodiments, a process for making a personal hygiene product comprises attaching at least a portion of a stretched elastic film to at least a portion of a non-woven layer via ultrasonic bonding to form a personal hygiene product preform, and applying one or a plurality of additional processing steps to the personal hygiene product preform to form the personal hygiene product.

In illustrative embodiments, a personal hygiene product comprises a stretched elastic film and a non-woven layer. At least a portion of the stretched elastic film is ultrasonically bonded to at least a portion of the non-woven layer.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which.

DETAILED DESCRIPTION

Figure 1:
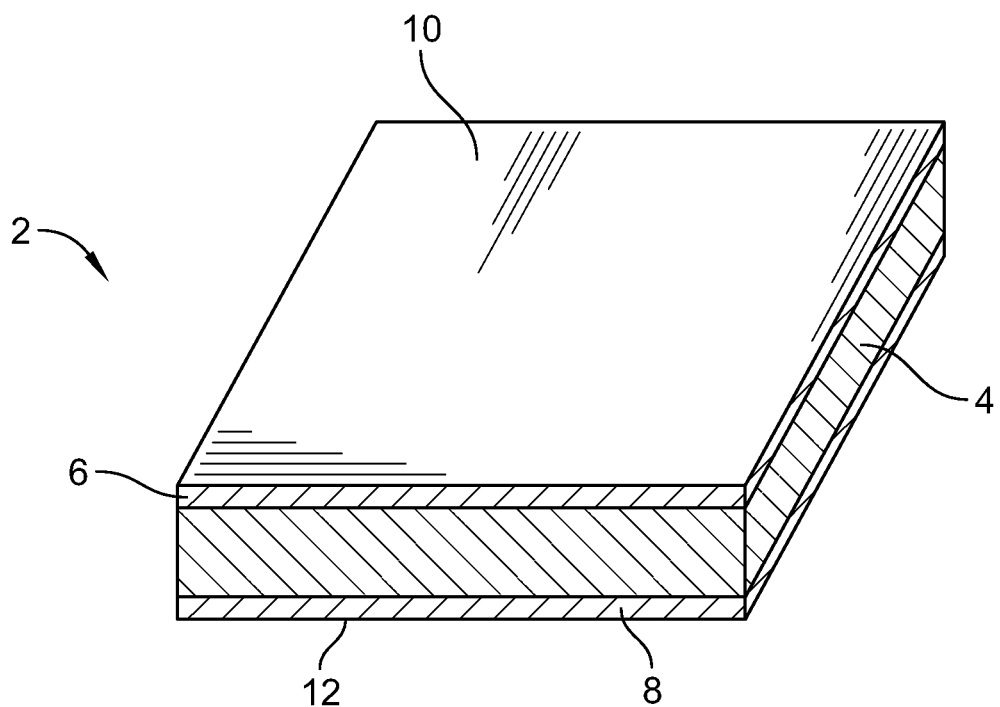
FIG. 1 is a diagrammatic view of a representative embodiment of a stretched elastic film that includes a core layer and two skin layers.

In some embodiments, the present disclosure provides a multi-layer stretched elastic film that includes a core layer interposed between one or more outer skin layers adjacent to the core layer. A first embodiment of a multi-layered stretched elastic film 2 in accordance with the present disclosure is shown, for example, in FIG. 1. The multilayer stretched elastic film 2 includes a core layer 4 interposed between a first skin layer 6 and a second skin layer 8. The first skin layer 6 has an outer surface 10 and the second skin layer 8 has an outer surface 12. Although the stretched elastic film 2 is shown in FIG. 1 as including the first skin layer 6 and the second skin layer 8, one or both of these two outer skin layers is optional and, in some embodiments, may not be present. Thus, in some embodiments, the present disclosure alternatively provides a monolayer stretched elastic film. A monolayer stretched elastic film in accordance with the present disclosure is analogous to the core layer 4 shown in FIG. 1 without the first skin layer 6 and the second skin layer 8.

The core layer 4 may include a thermoplastic polymer (or combination of thermoplastic polymers), whereas the outer skin layers 6 and 8 may have either the same composition as the core layer 4 or a different composition than the core layer 4. By way of example, one or both of the first skin layer 6 and the second skin layer 8 may contain a thermoplastic polymer or combination of thermoplastic polymers. The choice of the thermoplastic polymer or combination of thermoplastic polymers in each of the core layer 4, the first skin layer 6, and the second skin layer 8 shown is FIG. 1 is independent of the other layers.

In one example, a stretched elastic film 2 in accordance with the present disclosure is formed via a blown film process. In another example, a stretched elastic film 2 in accordance with the present disclosure is formed via a cast film process. The cast film process involves the extrusion of molten polymers through an extrusion die to form a thin film. The film is pinned to the surface of a chill roll with an air knife, an air blanket, and/or a vacuum box.

In illustrative embodiments, a process for making a stretched elastic film 2 in accordance with the present disclosure includes (a) extruding a composition containing a thermoplastic polymer to form a molten web, (b) casting the molten web against a surface of a chill roll using an air knife, an air blanket, a vacuum box, or a combination thereof to form a quenched film, and (c) stretching the quenched film in a machine direction in at least a 2:1 draw to form a stretched film. In some embodiments, the process for making a stretched elastic film 2 in accordance with the present disclosure optionally further includes relaxing the stretched film to form a relaxed film. In some embodiments, the process for making a stretched elastic film 2 in accordance with the present disclosure optionally further includes ageing the quenched film to form an aged film (which has an increased elasticity relative to the quenched film) prior to performing the stretching.

In illustrative embodiments, the extruding (a) comprises co-extruding at least a first composition, a second composition, and a third composition to form the molten web. The first composition forms at least one first film layer 4, the second composition forms at least one second film layer 6, and the third composition forms at least one third film layer 8, wherein the at least one first film layer 4 is disposed between the at least one second film layer 6 and the at least one third film layer 8. The first composition comprises a polyolefin, a styrene block copolymer, a non-styrene block copolymer, or a combination thereof, and the second composition and the third composition are identical or different.

It has been discovered that by pre-stretching the quenched film (e.g., in a machine direction in at least a 2:1 draw), recovery forces of the film are reduced, which may facilitate certain manufacturing steps (e.g., holding the elastic film against a vacuum shoe during a slip-cut step). Moreover, it has further been discovered that by using a vacuum box, blowing air (e.g., an air knife and/or an air blanket), or a vacuum box in combination with blowing air to cast the molten web against a chill roll in accordance with the present disclosure, stretched elastic films 2 exhibiting surprisingly and unexpectedly improved properties as compared to other elastic films may be prepared. As further described below, these properties may include reduced basis weight.

In some embodiments, the thermoplastic polymer-containing compositions may be extruded in a cast-embossed process with an engraved pattern (matte or less than about 2-mil depth). In other embodiments, the compositions may be extruded via a blown co-extrusion process. In illustrative embodiments, as further explained below, the film extrusion is performed using a vacuum box casting process, which circumvents the limitations of draw resonance that may affect embossed films, as well as bubble instability that may affect blown films.

Figure 2:
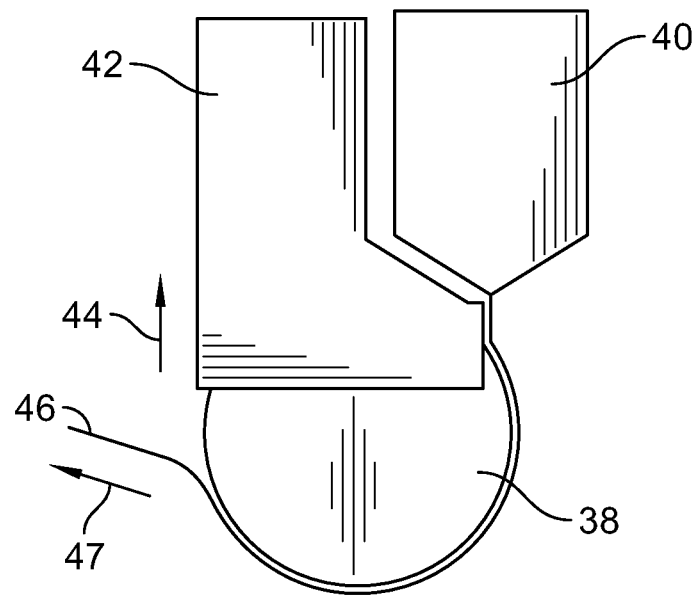
FIG. 2 is a diagrammatic view of an exemplary process for casting a molten web against a chill roll using a vacuum box.

In illustrative embodiments, the molten web is cast against the surface of the chill roll under negative pressure using a vacuum box as shown in simplified schematic form in FIG. 2. A vacuum box works by evacuating air between the film and the surface of the chill roll. For example, as shown in FIG. 2, a film 46 is extruded from an extrusion die 40 in the direction of arrow 47 and quenched from the molten state with a vacuum box 42. The vacuum box 42 draws a vacuum behind the molten web 46 in the direction of arrow 44 to draw the film 46 down onto the chill roll 38.

The vacuum drawn in the direction of arrow 44 removes the entrained air between the surface of the chill roll 38 and the film 46. The vacuum box process is not subject to draw resonance for high molecular weight polymers that would tend to extrude unstable thickness in a nipped quench process due to the draw resonance phenomenon.

When a vacuum box 42 is used, the molten polymer may exit the die 40 and hit the chill roll 38 within a smaller distance than in an embossed process. For example, in some embodiments, the melt curtain is configured to hit the chill roll 38 within a distance of less than about 12 inches, 11 inches, 10 inches, 9 inches, 8 inches, 7 inches, 6 inches, 5 inches, 4 inches, 3, inches, 2 inches, or 1 inch. In illustrative embodiments, the melt curtain is configured to exit the die and hit the roll within a distance of less than about 3 inches and, in some examples, within a distance of about or less than 1 inch. One advantage of reducing the distance between the die 40 and the roll surface 38 as compared to in a nipped quench process is that smaller distances are less susceptible to the phenomenon of neck-in. Neck-in refers to a reduction in width of the molten web that occurs as the web leaves the die. By drawing the film 46 onto a surface of the chill roll 38 over a short distance as shown in FIG. 2, the vacuum box 42 may enhance web cooling, facilitate higher line speeds, reduce film neck-in, and/or reduce drag at the lip exit.

Figure 3:
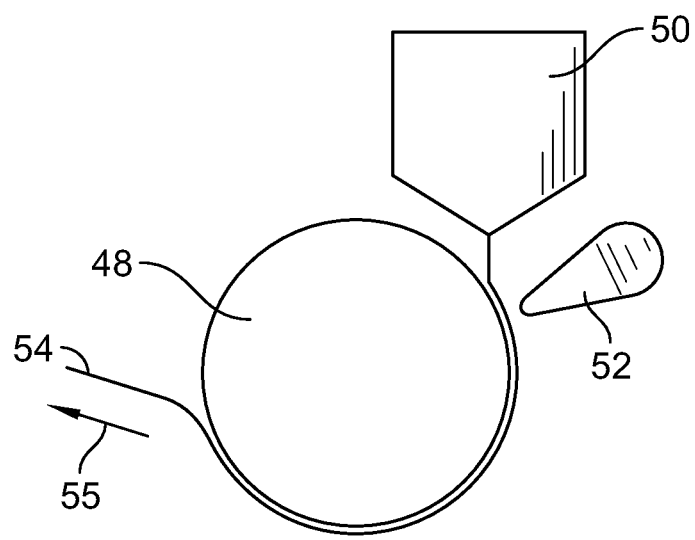
FIG. 3 is a diagrammatic view of an exemplary process for casting a molten web against a chill roll using an air knife.

In another example, the molten web is cast against the surface of the chill roll under positive pressure using an air knife or air blanket, as shown in simplified schematic form in FIG. 3. An air knife works to promote web quenching by gently blowing a high-velocity, low-volume air curtain over the molten film, thereby pinning the molten film to the chill roll for solidification. For example, as shown in FIG. 3, a film 54 is extruded from an extrusion die 50 in the direction of arrow 55 and quenched from the molten state with an air knife 52 blowing an air curtain over the molten film 54, thereby pinning the molten web 54 against a surface of the chill roll 48. An air blanket (a.k.a. "soft box") works similarly to an air knife and promotes web quenching by gently blowing an air curtain over the molten film. However, in the case of an air blanket, the air curtain is low velocity and high volume.

In a further example, the molten web is cast against the surface of the chill roll under a combination of negative pressure from a vacuum box, as shown in FIG. 2, and positive pressure from an air knife, as shown in FIG. 3. In illustrative embodiments, in the casting of the molten web against a surface of the chill roll, an exit temperature of cooling fluid passing through the chill roll is between about 50 degrees Fahrenheit and about 130 degrees Fahrenheit and, in some examples, between about 75 degrees Fahrenheit and about 130 degrees Fahrenheit.

Thermoplastic materials that have elastomeric properties are typically called elastomeric materials. Thermoplastic elastomeric materials are generally defined as materials that exhibit high resilience and low creep as though they were covalently crosslinked at ambient temperatures, yet process like thermoplastic non-elastomers and flow when heated above their softening point. The thermoplastic polymer 4 (or combination of thermoplastic polymers 4) used to make a stretched elastic film 2 in accordance with the present disclosure is not restricted, and may include all manner of thermoplastic polymers capable of being stretched.

In illustrative embodiments, the thermoplastic polymer is a polyolefin, (including but not limited to homopolymers, copolymers, terpolymers, and/or blends thereof), a non-styrene block copolymer, a styrene block copolymer, or a combination thereof.

Representative polyolefins that may be used in accordance with the present disclosure include but are not limited to low density polyethylene (LDPE), high density polyethylene (HDPE), linear low density polyethylene (LLDPE), ultra-low density polyethylene (ULDPE), medium density polyethylene, polypropylene, isotactic polypropylene, polybutylene, ethylene-propylene copolymers, polymers made using a single-site catalyst, ethylene maleic anhydride copolymers (EMAs), ethylene vinyl acetate copolymers (EVAs) such as those available under the trade designation ELVAX from E. I. DuPont de Nemours, Inc. (Wilmington, Del.), polymers made using Zeigler-Natta catalysts, styrene-containing block copolymers, ethylene acrylic acid copolymers, ethylene methacrylic acid copolymers such as those available under the trade designation SURLYN 1702 from E.I. DuPont de Nemours, Inc., polymethylmethacrylate, polystyrene, ethylene vinyl alcohol, and/or the like, and combinations thereof.

Methods for manufacturing LDPE are described in *The Wiley Encyclopedia of Packaging Technology*, pp. 753-754 (Aaron L. Brody et al. eds., 2nd Ed. 1997) and in U.S. Pat. No. 5,399,426, both of which are incorporated by reference herein, except that in the event of any inconsistent disclosure or definition from the present specification, the disclosure or definition herein shall be deemed to prevail.

ULDPE may be produced by a variety of processes, including but not limited to gas phase, solution and slurry polymerization as described in *The Wiley Encyclopedia of Packaging Technology*, pp. 748-50 (Aaron L. Brody et al. eds., 2nd Ed. 1997), incorporated by reference above, except that in the event of any inconsistent disclosure or definition from the present specification, the disclosure or definition herein shall be deemed to prevail.

ULDPE may be manufactured using a Ziegler-Natta catalyst, although a number of other catalysts may also be used. For example, ULDPE may be manufactured with a metallocene catalyst. Alternatively, ULDPE may be manufactured with a catalyst that is a hybrid of a metallocene catalyst and a Ziegler-Natta catalyst. Methods for manufacturing ULDPE are also described in U.S. Pat. Nos. 5,399,426, 4,668,752, 3,058,963, 2,905,645, 2,862,917, and 2,699,457, each of which is incorporated by reference herein in its entirety, except that in the event of any inconsistent disclosure or definition from the present specification, the disclosure or definition herein shall be deemed to prevail. The density of ULDPE is achieved by copolymerizing ethylene with a sufficient amount of one or more monomers. In illustrative embodiments, the monomers are selected from 1-butene, 1-hexene, 4-methyl-1-pentene, 1-octene, and combinations thereof. Methods for manufacturing polypropylene are described in *Kirk-Othmer Concise Encyclopedia of Chemical Technology*, pp. 1420-1421 (Jacqueline I. Kroschwitz et al. eds., 4th Ed. 1999), which is incorporated herein by reference, except that in the event of any inconsistent disclosure or definition from the present specification, the disclosure or definition herein shall be deemed to prevail.

In illustrative embodiments, a polyolefin for use in accordance with the present disclosure includes polyethylene, polypropylene, or a combination thereof. In one example, the polyethylene includes linear low density polyethylene which, in some embodiments, includes a metallocene polyethylene. In another example, the polyethylene includes a combination of linear low density polyethylene and low density polyethylene. In a further example, the polyolefin consists essentially of only linear low density polyethylene.

Representative non-styrene block copolymers (elastomers or plastomers) suitable for use in accordance with the present disclosure include but are not limited to ethylene copolymers. Representative ethylene copolymers include but are not limited to ethylene vinyl acetates; ethylene octane; ethylene butane; ethylene/propylene copolymer or propylene copolymer elastomers, such as those available under the trade designation VISTAMAXX® available from ExxonMobil (Irving, Tex.); ethylene/propylene/diene terpolymer elastomers; metallocene polyolefins, such as polyethylene, poly (1-hexane), copolymers of ethylene and 1-hexene, and poly(l-octene); thermoplastic elastomeric polyurethanes, such as that available under the trade designation MORTHANE PE44-203 polyurethane from Morton International, Inc. (Chicago, Ill.) and the trade designation ESTANE 58237 polyurethane from Noveon Corporation, Inc. (Cleveland, Ohio); polyvinyl ethers; poly-α-olefin-based thermoplastic elastomeric materials, such as those represented by the formula —$(CH_2CHR)_x$ where R is an alkyl group containing from about 2 to about 10 carbon atoms; poly-α-olefins based on metallocene catalysis, such as ENGAGE 8200, ethylene/poly-α-olefin copolymer available from Dow Plastics Co. (Midland, Mich.); polybutadienes; polybutylenes; polyisobutylenes such as VISTANEX NM L-80, available from Exxon Chemical Co.; polyether block amides such as PEBAX available from Elf Atochem North America, Inc. (Philadelphia, Pa.); and/or the like; and combinations thereof.

Thermoplastic elastomeric materials, in particular block copolymers, useful in accordance with the present disclosure include but are not limited to linear, radial, star, and tapered block copolymers, such as styrene block copolymers. Representative styrene block copolymers for use in accordance with the present disclosure include but are not limited to KRATON® or KRATON®-based styrene block copolymers available from Kraton Polymers, Inc. (Houston, Tex.), styrene-isoprene block copolymers, styrene-(ethylene-butylene) block copolymers, styrene-(ethylene-propylene) block copolymers, styrene-butadiene block copolymers, and/or the like, and combinations thereof. In some embodiments, thermoplastic elastomeric materials in accordance with the present disclosure include polyether esters such as those available under the trade designation HYTREL G3548 from E.I. DuPont de Nemours, and/or polyether block amides such as those available under the trade designation PEBAX from Elf Atochem.

Additional thermoplastic materials which may be used in accordance with the present disclosure include but are not limited to polyesters including amorphous polyester, polyamides, fluorinated thermoplastics such as polyvinylidene fluoride; halogenated thermoplastics such as chlorinated polyethylene, polyether-block-amides such as those available under the trade designation PEBAX 5533 from ElfAtochem, and/or the like, and combinations thereof.

Figure 4:
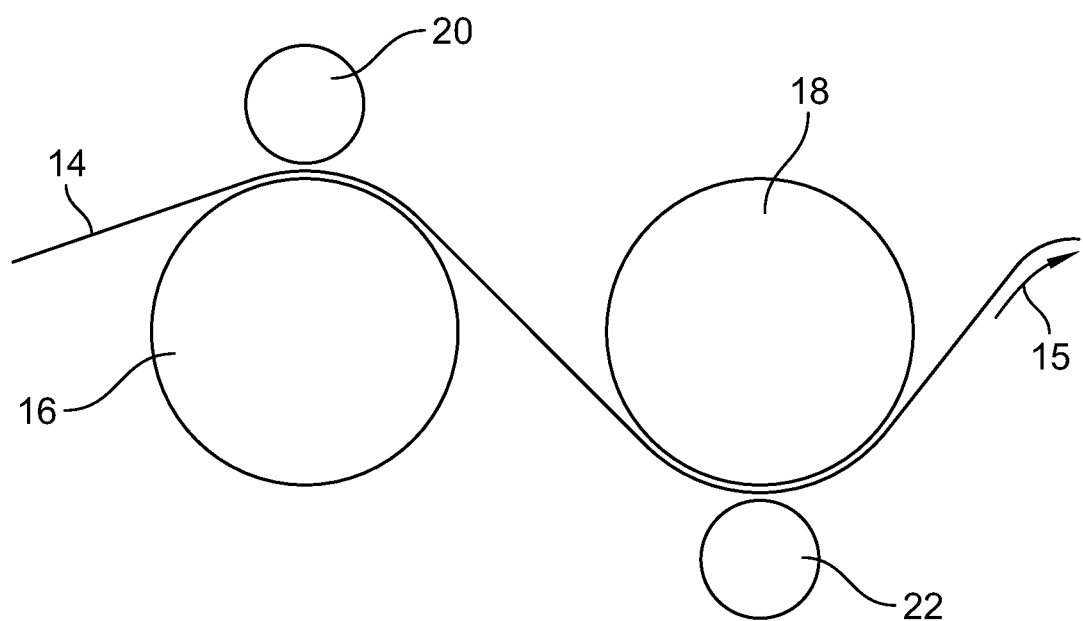
FIG. 4 is a diagrammatic view of an exemplary process for machine direction (MD) stretching of a polymeric film.

A precursor film containing a thermoplastic polymer that is stretched, relaxed, and stretched to form a stretched elastic film 2 in accordance with the present disclosure may be prepared by mixing together the thermoplastic polymer (or a combination of thermoplastic polymers) and any optional components until blended, heating the mixture, and then extruding the mixture to form a molten web. A suitable film-forming process may be used to form a precursor film en route to forming a stretched elastic film. For example, the precursor film may be manufactured by casting or extrusion using blown-film, co-extrusion, or single-layer extrusion techniques and/or the like. In one example, the precursor film may be wound onto a winder roll for subsequent stretching in accordance with the present disclosure (e.g., following optional ageing of the quenched film to allow for elasticity of the film to increase over time). In another example, the precursor film may be manufactured in-line with a film stretching apparatus such as shown in FIG. 4.

In addition to containing one or more thermoplastic polymers, the precursor film may also contain other optional components to improve the film properties or processing of the film. Representative optional components include but are not limited to anti-oxidants (e.g., added to prevent polymer degradation and/or to reduce the tendency of the film to discolor over time) and processing aids (e.g., added to facilitate extrusion of the precursor film). In one example, the amount of one or more anti-oxidants in the precursor film is less than about 1% by weight of the film and the amount of one or more processing aids is less than about 5% by weight of the film. Additional optional additives include but are not limited to whitening agents (e.g., titanium dioxide), which may be added to increase the opacity of the film. In one example, the amount of one or more whitening agents is less than about 10% by weight of the film. Further optional components include but are not limited to antiblocking agents (e.g., diatomaceous earth) and slip agents (e.g. erucamide a.k.a. erucylamide), which may be added to allow film rolls to unwind properly and to facilitate secondary processing (e.g., diaper making). In one example, the amount of one or more antiblocking agents and/or one or more slip agents is less than about 5% by weight of the film. Further additional optional additives include but are not limited to scents, deodorizers, pigments other than white, noise reducing agents, and/or the like, and combinations thereof. In one example, the amount of one or more scents, deodorizers, pigments other than white, and/or noise reducing agents is less than about 10% by weight of the film.

The type of stretching used to transform a quenched film into a stretched elastic film 2 in accordance with the present disclosure is not restricted. All manner of stretching processes—and combinations of stretching processes are contemplated for use. In illustrative embodiments, the stretching includes MD stretching. In other examples, the stretching may include one or more of CD IMG stretching, MD IMG stretching, cold draw, and/or the like.

In illustrative embodiments, the type of stretching used to transform a quenched film into a stretched elastic film 2 in accordance with the present disclosure includes MD stretching. In addition, in illustrative embodiments, at least a portion of the MD stretching is performed at ambient temperature (i.e., room temperature). In some embodiments, the stretching in the machine direction is in at least a 3:1 draw and, in other embodiments, in at least a 4:1 draw.

In one example, stretching may be achieved via machine direction (MD) orientation by a process analogous to that shown in simplified schematic form in FIG. 4. For example, the film 14 shown in FIG. 4 may be passed between at least two pairs of rollers in the direction of an arrow 15. In this example, first roller 16 and a first nip 20 run at a slower speed ($V_1$) than the speed ($V_2$) of a second roller 18 and a second nip 22. The ratio of $V_2/V_1$ determines the degree to which the film 14 is stretched. Since there may be enough drag on the roll surface to prevent slippage, the process may alternatively be run with the nips open. Thus, in the process shown in FIG. 4, the first nip 20 and the second nip 22 are optional.

Figure 5:
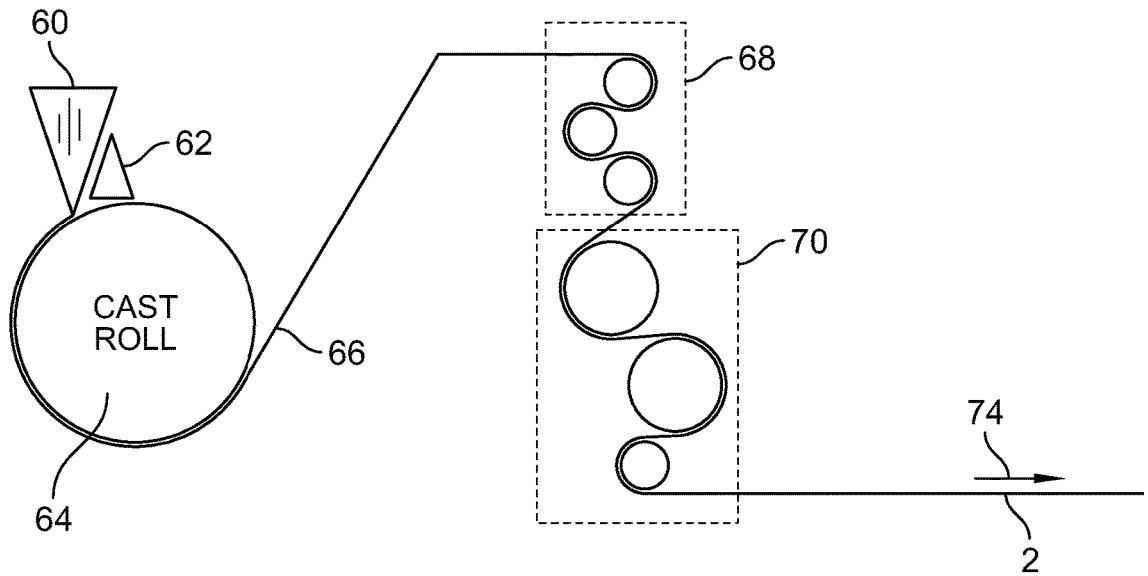
FIG. 5 is a diagrammatic view of an exemplary in-line process for extruding, quenching, stretching, and relaxing a polymeric film.

In illustrative embodiments, a process for making a stretched elastic film 2 in accordance with the present disclosure may be executed as shown in simplified schematic form in FIG. 5. The process includes extruding a composition containing a thermoplastic polymer 4 from a die 60 to form a molten web. The molten web is cast against a surface of a chill roll 64 under negative pressure from a vacuum box 62 to form a quenched film 66. The quenched film 66 is stretched by MD stretching from a series of rollers moving at different speeds (e.g., machine direction stretching) at an MD stretching station 68, and subsequently relaxed at an MD relaxation station 70. The MD-relaxed film exits MD relaxing station 70 to form a stretched elastic film 2 in accordance with the present disclosure. The stretched elastic film 2 exiting the relaxing station 70 in the direction 74 may be sent for winding.

In the MD stretching station 68, the elastic co-extrusion is stretched in a series of three closely spaced rolls with nips. In illustrative embodiments, the film is stretched 100% (2:1) between the first and second roll and an additional 100% (2:1) between the second and third roll. Thus, the total stretch is 4:1 (2×2).

In the relaxing station 70, the speed of downstream rolls is reduced to allow the web to nearly relax and be wound up. Somewhere within the area of relaxation, optional perforation may be implemented via a slitting station (not shown).

As shown in FIG. 5, the extruding, the casting, the stretching, and the relaxing are all achieved via in-line processing. However, this is not required. In some embodiments, it may be beneficial to perform the stretching in an out-of-line operation. The reason is that some elastic materials may need extra time after extrusion to achieve their full elastic potential. As a result, any break issues or downtime may be less costly in an out-of-line operation. Therefore, in some embodiments, it may be advantageous to age the quenched film to form an aged film prior to performing the stretching. For example, some elastomeric materials (e.g., polypropylene-based elastomers such as those sold under the trade designation VISTAMAXX) may require additional time to crystallize in order to achieve optimum elasticity. For such materials, the aged film has increased elasticity relative to the quenched film, and better results may be obtained when stretching is performed on the aged film.

In some embodiments, the extruding and the casting are achieved via in-line processing, and one or more of the stretching and the relaxing is achieved via post-processing of the quenched film. In other embodiments, at least the extruding, the casting, and the stretching are achieved via in-line processing. In further embodiments, each of the extruding, the casting, the stretching, and the relaxing are achieved via in-line processing.

Prior to stretching, the precursor film may have an initial basis weight of less than about 100 grams per square meter (gsm). In one example, the precursor film has an initial basis weight of less than about 75 gsm. The precursor film may be a monolayer film, in which case the entire precursor film comprises the thermoplastic polymer (or combination of thermoplastic polymers). In another example, the precursor film may be a multilayer film as suggested in FIG. 1.

In illustrative embodiments, as noted above, a stretched elastic film 2 prepared in accordance with the present disclosure (e.g., by using a vacuum box and/or air knife to cast a molten web containing a thermoplastic polymer (e.g., an elastomer) against a chill roll) may have reduced basis weight as compared to conventional stretched elastic films.

The basis weight of a stretched elastic film 2 in accordance with the present disclosure, after relaxation, may be varied based on a desired end use (e.g., the desired properties and/or applications of the stretched elastic film). In one example, the basis weight, after relaxation, ranges from about 5 gsm to about 30 gsm. In another example, the basis weight, after relaxation, ranges from about 6 gsm to about 25 gsm. In some examples, the basis weight, after relaxation, is less than about 50 gsm and, in illustrative embodiments, less than about 45 gsm, 40 gsm, 35 gsm, 30 gsm, 25 gsm, or 20 gsm. In illustrative embodiments, the basis weight, after relaxation, is between about 20 gsm and about 30 gsm. Although basis weights outside this range may also be employed (e.g., basis weights above about 30 gsm), lower basis weights minimize material cost as well as maximize consumer satisfaction (e.g., a thinner film may provide increased comfort to the user of a personal hygiene product that includes the film). The basis weight of a stretched elastic film 2 in accordance with the present disclosure may be one of several different values or fall within one of several different ranges. For example, it is within the scope of the present disclosure to select a basis weight, after relaxation, to be one of the following values: about 30 gsm, 29 gsm, 28 gsm, 27 gsm, 26 gsm, 25 gsm, 24 gsm, 23 gsm, 22 gsm, 21 gsm, 20 gsm, 19 gsm, 18 gsm, 17 gsm, 16 gsm, 15 gsm, 14 gsm, 13 gsm, 12 gsm, 11 gsm, 10 gsm, 9 gsm, 8 gsm, 7 gsm, 6 gsm, or 5 gsm.

It is also within the scope of the present disclosure for the basis weight of the stretched elastic film 2 to fall within one of many different ranges. In a first set of ranges, the basis weight of the stretched elastic film 2, after relaxation, is in one of the following ranges: about 5 gsm to 30 gsm, 6 gsm to 30 gsm, 7 gsm to 30 gsm, 8 gsm to 30 gsm, 9 gsm to 30 gsm, 10 gsm to 30 gsm, 11 gsm to 30 gsm, 12 gsm to 30 gsm, 13 gsm to 30 gsm, and 14 gsm to 30 gsm. In a second set of ranges, the basis weight of the stretched elastic film, after relaxation, is in one of the following ranges: about 5 gsm to 29 gsm, 5 gsm to 28 gsm, 5 gsm to 27 gsm, 5 gsm to 26 gsm, 5 gsm to 25 gsm, 5 gsm to 24 gsm, 5 gsm to 23 gsm, 5 gsm to 22 gsm, 5 gsm to 21 gsm, 5 gsm to 20 gsm, 5 gsm to 19 gsm, 5 gsm to 18 gsm, 5 gsm to 17 gsm, 5 gsm to 16 gsm, 5 gsm to 15 gsm, 5 gsm to 14 gsm, 5 gsm to 13 gsm, 5 gsm to 12 gsm, 5 gsm to 11 gsm, 5 gsm to 10 gsm, 5 gsm to 9 gsm, 5 gsm to 8 gsm, and 5 gsm to 7 gsm. In a third set of ranges, the basis weight of the stretched elastic film 2, after relaxation, is in one of the following ranges: about 6 gsm to 29 gsm, 7 gsm to 29 gsm, 7 gsm to 28 gsm, 7 gsm to 27 gsm, 7 gsm to 26 gsm, 7 gsm to 25 gsm, 7 gsm to 24 gsm, 7 gsm to 23 gsm, 7 gsm to 22 gsm, 7 gsm to 21 gsm, 7 gsm to 20 gsm, 7 gsm to 19 gsm, 7 gsm to 18 gsm, 7 gsm to 17 gsm, 7 gsm to 16 gsm, 7 gsm to 15 gsm, 7 gsm to 14 gsm, and 7 gsm to 13 gsm.

In illustrative embodiments, a stretched elastic film 2 in accordance with the present disclosure, after relaxation, exhibits a load at 100% that is less than that of a comparative stretched elastic film prepared without the pre-stretching. The basis weight of a stretched elastic film 2 in accordance with the present disclosure may be varied based on a desired load at 100%. By way of illustration, in some cases, a stretched elastic film 2 in accordance with the present disclosure, after relaxation, has a basis weight of about 30 gsm and a load at 100% of less than about 250 grams/inch. In other cases, a stretched elastic film 2 in accordance with the present disclosure, after relaxation, has a basis weight of about 30 gsm and a load at 100% of less than about 200 grams/inch. In further cases, a stretched elastic film 2 in accordance with the present disclosure, after relaxation, has a basis weight of about 30 gsm and a load at 100% of less than about 150 grams/inch. In still further cases, a stretched elastic film 2 in accordance with the present disclosure, after relaxation, has a basis weight of about 30 gsm and a load at 100% of less than about 125 grams/inch.

The load at 100% of a stretched elastic film 2 in accordance with the present disclosure may be one of several different values or fall within one of several different ranges. For example, for a stretched elastic film having a basis weight of less than or equal to about 30 gsm—in some embodiments, less than or equal to about 25 gsm or 20 gsm—it is within the scope of the present disclosure to select a load at 100%, after relaxation, to be less than or equal to one of the following values: about 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, 200%, 201%, 202%, 203%, 204%, 205%, 206%, 207%, 208%, 209%, 210%, 211%, 212%, 213%, 214%, 215%, 216%, 217%, 218%, 219%, 220%, 221%, 222%, 223%, 224%, 225%, 226%, 227%, 228%, 229%, 230%, 231%, 232%, 233%, 234%, 235%, 236%, 237%, 238%, 239%, 240%, 241%, 242%, 243%, 244%, 245%, 246%, 247%, 248%, 249%, 250%, 251%, 252%, 253%, 254%, 255%, 256%, 257%, 258%, 259%, 260%, 261%, 262%, 263%, 264%, 265%, 266%, 267%, 268%, 269%, 270%, 271%, 272%, 273%, 274%, 275%, 276%, 277%, 278%, 279%, 280%, 281%, 282%, 283%, 284%, 285%, 286%, 287%, 288%, 289%, 290%, 291%, 292%, 293%, 294%, 295%, 296%, 297%, 298%, 299%, or 300%.

It is also within the scope of the present disclosure for the load at 100% of the stretched elastic film 2 to fall within one of many different ranges. In a first set of ranges, the load at 100%, after relaxation, for a stretched elastic film having a basis weight of less than or equal to about 30 gsm—in some embodiments, less than or equal to about 25 gsm or 20 gsm—is in one of the following ranges: about 75% to 350%, 75% to 345%, 75% to 340%, 75% to 335%, 75% to 330%, 75% to 325%, 75% to 320%, 75% to 315%, 75% to 310%, 75% to 305%, 75% to 300%, 75% to 295%, 75% to 290%, 75% to 285%, 75% to 280%, 75% to 275%, 75% to 270%, 75% to 265%, 75% to 260%, 75% to 255%, 75% to 250%, 75% to 245%, 75% to 240%, 75% to 235%, 75% to 230%, 75% to 225%, 75% to 220%, 75% to 215%, 75% to 210%, 75% to 205%, 75% to 200%, 75% to 195%, 75% to 190%, 75% to 185%, 75% to 180%, 75% to 175%, 75% to 170%, 75% to 165%, 75% to 160%, 75% to 155%, 75% to 150%, 75% to 145%, 75% to 140%, 75% to 135%, 75% to 130%, and 75% to 125%. In a second set of ranges, the load at 100%, after relaxation, for a stretched elastic film having a basis weight of less than or equal to about 30 gsm—in some embodiments, less than or equal to about 25 gsm or 20 gsm—is in one of the following ranges: about 76% to 300%, 77% to 300%, 78% to 300%, 79% to 300%, 80% to 300%, 81% to 300%, 82% to 300%, 83% to 300%, 84% to 300%, 85% to 300%, 86% to 300%, 87% to 300%, 88% to 300%, 89% to 300%, 90% to 300%, 91% to 300%, 92% to 300%, 93% to 300%, 94% to 300%, 95% to 300%, 96% to 300%, 97% to 300%, 98% to 300%, 99% to 300%, 100% to 300%, 101% to 300%, 102% to 300%, 103% to 300%, 104% to 300%, 105% to 300%, 106% to 300%, 107% to 300%, 108% to 300%, 109% to 300%, 110% to 300%, 111% to 300%, 112% to 300%, 113% to 300%, 114% to 300%, 115% to 300%, 116% to 300%, 117% to 300%, 118% to 300%, 119% to 300%, 120% to 300%, 121% to 300%, 122% to 300%, 123% to 300%, 124% to 300%, 125% to 300%, 126% to 300%, 127% to 300%, 128% to 300%, 129% to 300%, 130% to 300%, 131% to 300%, 132% to 300%, 133% to 300%, 134% to 300%, 135% to 300%, 136% to 300%, 137% to 300%, 138% to 300%, 139% to 300%, 140% to 300%, 141% to 300%, 142% to 300%, 143% to 300%, 144% to 300%, 145% to 300%, 146% to 300%, 147% to 300%, 148% to 300%, 149% to 300%, and 150% to 300%. In a third set of ranges, the load at 100%, after relaxation, for a stretched elastic film having a basis weight of less than or equal to about 30 gsm—in some embodiments, less than or equal to about 25 gsm or 20 gsm—is in one of the following ranges: about 75% to 225%, 80% to 220%, 85% to 215%, 90% to 210%, 95% to 205%, 100% to 200%, 105% to 195%, 110% to 190%, 115% to 180%, and 120% to 175%.

In some embodiments, as shown in FIG. 1, the present disclosure provides a multi-layer stretched elastic film 2. In other embodiments, as noted above, the present disclosure provides a monolayer stretched elastic film 2 (i.e., core layer 4 in FIG. 1 without the outer skin layers 6 and 8). In one example, the skin layers may be independently selected from compositions designed to minimize the levels of volatiles building up on the extrusion die. In one example, a pair of skin layers sandwiching a core layer are relatively thin and together account for no more than about 30% of the total film thickness. In some embodiments, the skin layer may be breathable even if perforation is not performed. For example, the skin layer may include one or more discontinuities that are introduced during the stretching process. The likelihood of discontinuities forming in a skin layer may increase as the thickness of the skin layer subjected to stretching decreases.

In one example, a multi-layer stretched elastic film in accordance with the present disclosure may be manufactured by feed block co-extrusion. In another example, a multi-layer stretched elastic film in accordance with the present disclosure may be made by blown film (tubular) co-extrusion. Methods for feed block and blown film extrusion are described in *The Wiley Encyclopedia of Packaging Technology*, pp. 233-238 (Aaron L. Brody et al. eds., 2nd Ed. 1997), which is incorporated herein by reference, except that in the event of any inconsistent disclosure or definition from the present specification, the disclosure or definition herein shall be deemed to prevail. Methods for film extrusion are also described in U.S. Pat. No. 6,265,055, the entire contents of which are likewise incorporated by reference herein, except that in the event of any inconsistent disclosure or definition from the present specification, the disclosure or definition herein shall be deemed to prevail.

In some embodiments, as described above, the present disclosure provides stretched elastic films (e.g., mono-layer or multi-layer). In other embodiments, the present disclosure further provides elastic films that are not stretched but which contain a folded edge that provides tear-resistance to the film.

Figure 6:
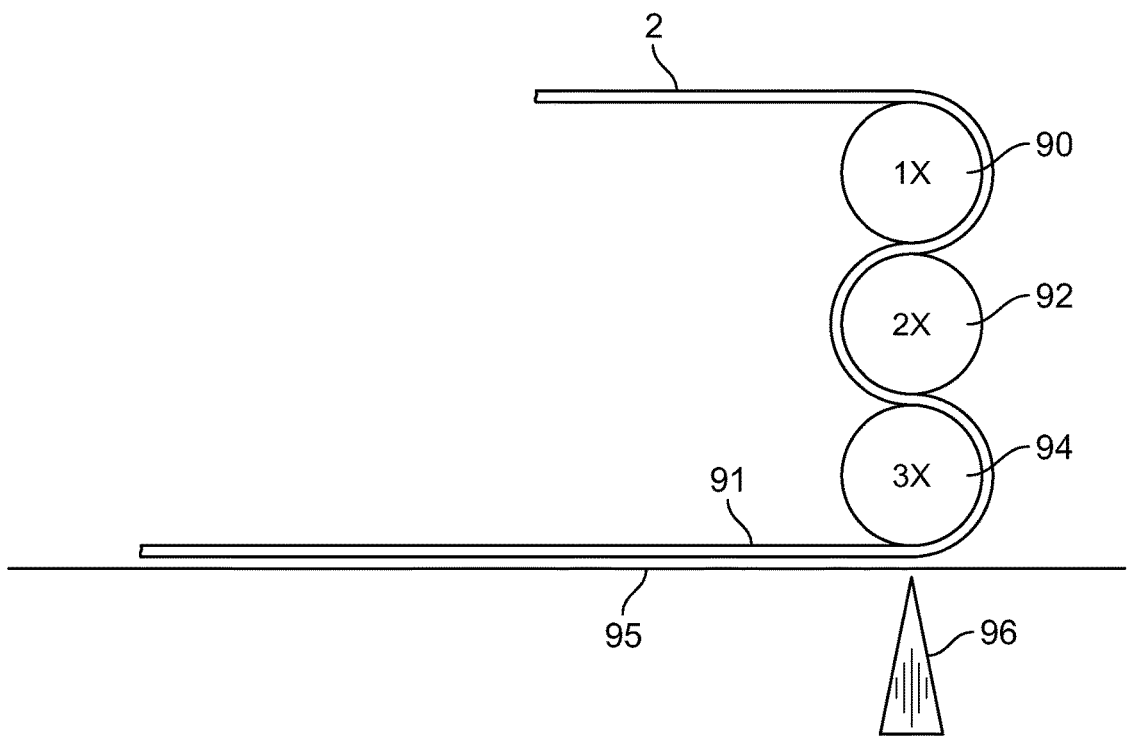
FIG. 6 is a diagrammatic view of a representative process for post-stretching a stretched elastic film and ultrasonically bonding the post-stretched stretched elastic film to a non-woven material.

In illustrative embodiments, as shown in FIG. 6, a stretched elastic film 2 in accordance with the present disclosure may be subjected to additional post-stretching (e.g., by an end user of the film). In the exemplary process shown in FIG. 6, the stretched elastic film 2 may be post-stretched in a machine direction by further MD stretching from a series of additional rollers moving at different speeds. For example, a first roller 90 (1×), a second roller 92 (2×), and a third roller 94 (3×) may be used to post-stretch the film in a machine direction. In some embodiments, the resultant post-stretched film 91 may be ultrasonically bonded to a non-woven material 95 by an ultrasonic bond horn 96.

In some embodiments, a stretched elastic film in accordance with the present disclosure may be used as a replacement for synthetic fibers, such as those conventionally used in the waistbands and/or curved elastic leg gathers of incontinence briefs, diapers, training pants, and/or the like. Synthetic fibers commonly used in pants-type personal hygiene products include the polyurethane spandex fibers sold under the tradename LYCRA by Invista (Wichita, Kans.). Since LYCRA strands and conventional non-woven materials typically have different melting temperatures and are therefore thermally incompatible, adhesive is generally needed to attach LYCRA strands to non-woven materials.

In illustrative embodiments, stretched elastic films in accordance with the present disclosure may be used as replacements for LYCRA strands in applications including but not limited to personal hygiene products. By replacing the LYCRA strands that conventionally form the "belly panel" of incontinence pants with an elastic film in accordance with the present disclosure, elastic panels with a much flatter appearance may be generated. Moreover, a stretched elastic film in accordance with the present disclosure may be configured to distribute pressure over a wider area than the small area of a LYCRA fiber circumference, thus minimizing and/or eliminating red marks caused by the constriction of small blood vessels in the skin. With the wide flat application of a stretched elastic film, the same or comparable force may be applied to allow the elastic to perform its fit and leakage prevention functions without cutting off blood flow.

In addition, a stretched elastic film in accordance with the present disclosure may be configured to have a thermally compatible melting temperature with that of a non-woven material. As a result, the stretched elastic film may be thermally or ultrasonically bonded to the non-woven material without the use of any adhesive. In illustrative embodiments, stretched elastic films and the non-woven materials may be attached via ultrasonic bonding. For example, one or both of first skin layer 6 and second skin layer 8 of a stretched elastic film 2 in accordance with the present disclosure may be selected to be thermally compatible with the non-woven layer. Thus, if the non-woven material is homopolymer polypropylene (160° C. to 165° C. melt temperature), one or both of first skin layer 6 and second skin layer 8 may be selected have the same melt temperature. In alternative embodiments, if the non-woven material is polyethylene or bico (polyethylene sheath on PP core) nonwoven, the stretched elastic film 2 may be selected to have a polyethylene-rich first skin layer 6 and/or second skin layer 8.

Figure 7:
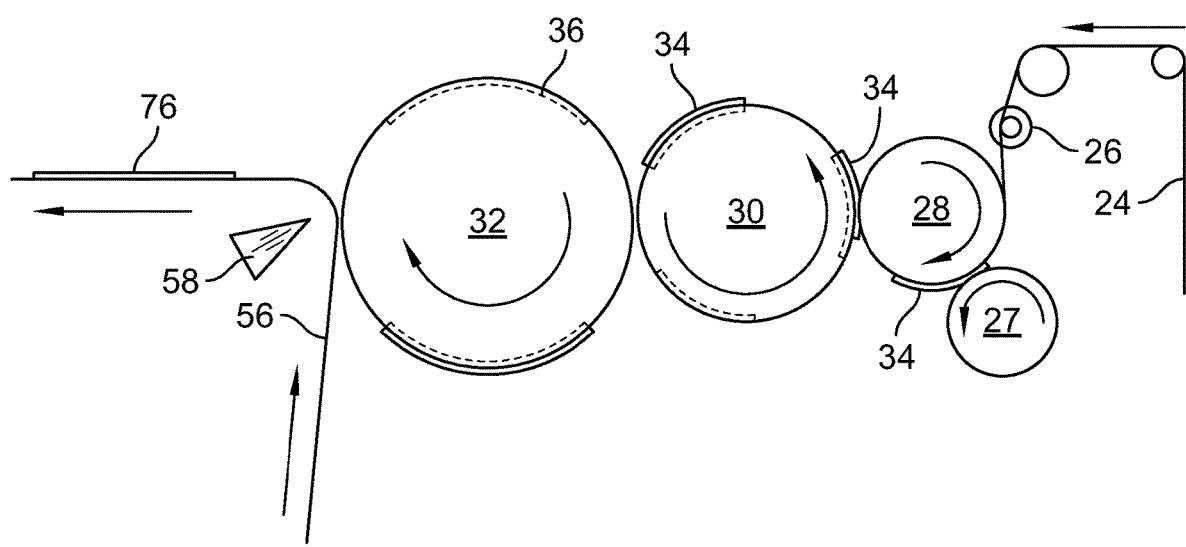
FIG. 7 is a diagrammatic view of a representative process for ultrasonically bonding non-continuous segments of a stretched elastic film to a non-woven material.

In a first illustrative application in accordance with the present disclosure, a stretched elastic film in accordance with the present disclosure may be used in a slip-cut process, as shown in FIG. 7, to apply film at intermittent positions along a non-woven substrate. The representative process shown in FIG. 7 is analogous to one shown and described in U.S. Pat. No. 8,673,098 B2, the entire contents of which are incorporated by reference herein, except that in the event of any inconsistent disclosure or definition from the present specification, the disclosure or definition herein shall be deemed to prevail.

As shown in FIG. 7, the film 24—which, in some embodiments, is an un-stretched quenched film and, in other embodiments, is a pre-stretched elastic film 2—is fed to a clamp collar 26 and then cut into segments 34 between a slip-cut anvil roll 28 and a knife roll 27. The segments 34 are transferred to a set pitch roller 30 and then a rotating vacuum wheel 32 containing vacuum regions 36. A non-woven material 56 traveling in the direction shown is configured to receive the segments 34 of stretched elastic film, each of which is bonded to the non-woven material 56 by ultrasonic bonding through the use of an ultrasonic horn 58, thereby producing the ultrasonically bonded multi-layer article 76.

As shown in FIG. 7, the segments 34 of stretched elastic film are placed intermittently on the non-woven material 56 as opposed to in a continuous fashion. One of the difficulties in using spandex threads in a slip-cut operation is that it is very difficult to hold the strands in place during transfer. By contrast, a stretched elastic film 34 in accordance with the present teachings may be gripped with a vacuum 36 and held in place during the transfer. Moreover, by pre-stretching the elastic film 24 before subjecting the film 24 to a cutting operation and transferring the cut segments to the vacuum shoe 36, the forces are reduced and less overall stretch is needed. In illustrative embodiments, intermittently applied stretched elastic film may be used in trainer pants in which elasticity is typically not provided around the entire circumference of the waistband but rather only at selection portions (e.g., on the sides).

Figure 8:
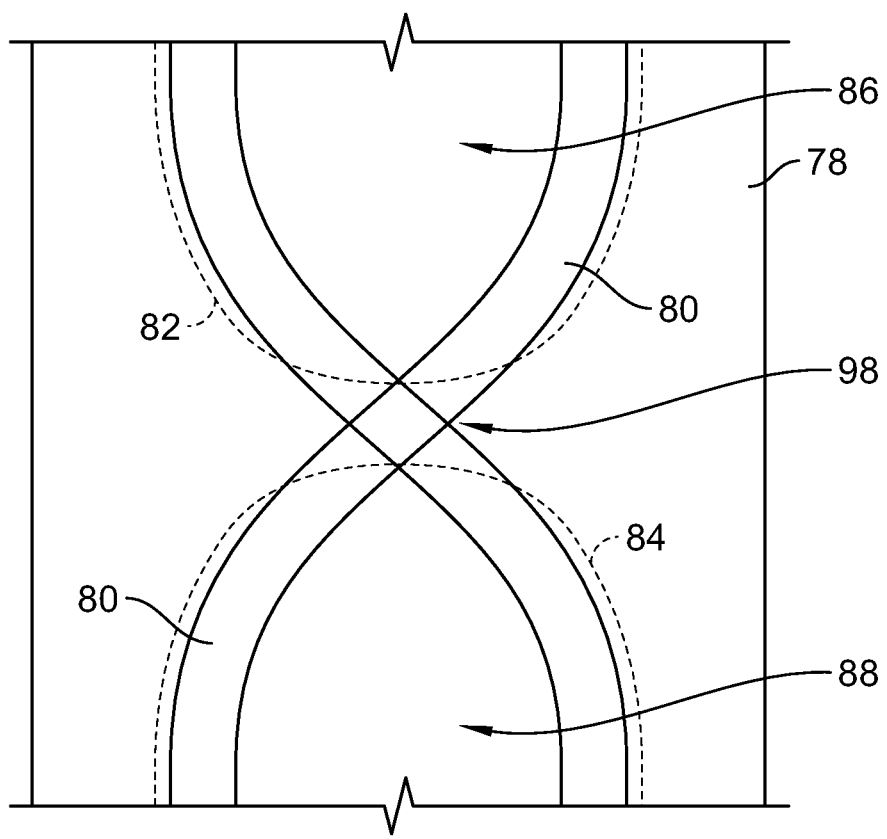
FIG. 8 is a diagrammatic view of a representative process for applying a stretched elastic film to a non-woven material in a curved configuration.

In a second illustrative application in accordance with the present disclosure, a stretched elastic film in accordance with the present disclosure may be used to form the curved elastic leg gathers of a pants-type personal hygiene product by applying the stretched elastic film to a non-woven substrate in a sinusoidal pattern, as shown in FIG. 8. The representative pattern shown in FIG. 8 is analogous to one shown and described in U.S. Pat. No. 6,482,278 B1, and may be applied to the non-woven substrate using an analogous procedure (e.g., an oscillating, pendulum type application process). The entire contents of U.S. Pat. No. 6,482,278 B1 are incorporated by reference herein, except that in the event of any inconsistent disclosure or definition from the present specification, the disclosure or definition herein shall be deemed to prevail.

As shown in FIG. 8, a stretched elastic film 80 is applied to a non-woven material 78 in a sinusoidal pattern at a first portion 82 and a second portion 84. The first portion 82 and the second portion 84 correspond, respectively, to a first leg-hole 86 and a second leg-hole 88 of a pants-type personal hygiene product. The stretched elastic film 80 may be ultrasonically bonded to the non-woven material 78 through the use of an ultrasonic horn in the first portion 82 and the second portion 84. In the crotch region 98, any stretched elastic film 30 that is present may be relaxed simply by applying heat (e.g., 150° F. to 250° F.) in that region. Alternatively, the stretched elastic film 30 in the crotch region 98 may also be relaxed by using an ultrasonic horn and a flat roll.

The first leg-hole 86 and the second leg-hole 88 shown in FIG. 8 may already be present on the preform or formed subsequently through a cutting operation. In general, additional processing steps that can be applied to a personal hygiene product preform in accordance with the present disclosure include but are not limited to cutting, gluing, ultrasonically bonding, heating, cooling, thermal welding, folding, printing, or a combination thereof.

One of the difficulties in using spandex threads in a curved elastic leg application such as the one shown in FIG. 8 is being able to apply the individual spandex threads in the desired locations without spread using the oscillating motion of a pendulum applicator. Another even greater challenge is applying adhesive to the regions where the spandex strands actually end up in the final product without wasting adhesive. By contrast, a stretched elastic film in accordance with the present disclosure may be thermally or ultrasonically bonded to a non-woven material, thereby avoiding the spreading of spandex strands that occurs in the oscillating motion. More significantly, the use of adhesive may be avoided altogether, which results in significant cost savings and simplified processing.

In some embodiments, a multi-layer film in accordance with the present disclosure may contain one or a plurality of stretched elastic film layers analogous to the core layer 4 shown in FIG. 1. The individual film layers in a multi-layer film structure in accordance with the present disclosure may be monolayers or co-extrusions. Each of the individual stretched elastic film layers may be placed in any order within the inner layers of the multi-layer film structure. When a plurality of individual stretched elastic film layers in accordance with the present disclosure is used, the individual layers may differ from each other in thickness and/or type of thermoplastic polymer.

Multi-layer films of a type described above are not limited to any specific kind of film structure. Other film structures may achieve the same or similar result as the three-layer stretched elastic film layer 2 shown in FIG. 1. Film structure is a function of equipment design and capability. For example, the number of layers in a film depends only on the technology available and the desired end use for the film. Representative examples of film structures that may be implemented in accordance with the present disclosure include but are not limited to the following, wherein "A" represents a stretched elastic film layer in accordance with the present disclosure, and "B" represents an additional film layer (which, in some embodiments, is an additional stretched elastic film layer in accordance with the present disclosure):

A-B-A
A-A-B-A
A-B-A-A
A-A-B-A-A
A-B-A-A-A
A-B-A-B-A
A-B-A-A-A-A-A
A-A-B-A-A-A-A
A-A-A-B-A-A-A
A-B-A-A-A-B-A
A-B-A-A-B-A-A
A-B-A-B-A-A-A
A-B-A-B-A-B-A
A-B-A-A-A-A-A
A-A-B-A-A-A-A
A-A-A-B-A-A-A
A-B-A-A-A-B-A.

In the above-described exemplary film structures, each of the elastic film layers A may include two or more elastic film layers in order to better control other film properties, such as the ability to bond to nonwovens. For example, when there are two stretched elastic film layers in one "A" elastic film layer, and when "C" represents the second elastic film layer, some exemplary film structures are as follows:

A-C-B-C-A
A-C-A-C-B-C-A
A-C-B-C-A-C-A
A-C-A-C-B-C-A-C-A
A-C-B-C-A-C-A-C-A
A-C-B-C-A-B-C-A

Additionally, die technology that allows production of multiple layers in a multiplier fashion may be used. For example, an ABA structure may be multiplied from about 10 to about 1000 times. The resulting 10-time multiplied ABA structure may be expressed as follows:
A-B-A-A-B-A-A-B-A-A-B-A-A-B-A-A-B-A-A-B-A-A-B-A-A-B-A-A-B-A In some embodiments, as described above, the present disclosure provides stretched elastic films 2 (e.g., mono-layer or multi-layer). In other embodiments, the present disclosure further provides personal hygiene products containing one or more stretched elastic films (e.g., mono-layer or multi-layer) in accordance with the present disclosure.

In some embodiments, a multi-layer structure in accordance with the present teachings, such as the stretched elastic film 2 shown in FIG. 1, is a co-extrusion with a target layer ratio of about 7.5/85/7.5. In other embodiments, the multi-layer structure is a co-extrusion with a target layer ratio of about 10/80/10. In further embodiments, the multi-layer structure is a co-extrusion with a target layer ratio of about 5/90/5.

In illustrative embodiments, the core layer 4 shown in FIG. 2—which may be a single layer or multiple co-extruded layers—contains an elastomer-rich formula. The types of elastomers suitable for use in the core layer 4 range from polyolefin to block copolymer. Representative elastomers include but are not limited to the polypropylene elastomer available under the trade designation VISTAMAXX, the polyethylene block copolymer elastomer available under the trade designation INFUSE, and/or a combination thereof. In some embodiments, the core layer 4 contains a styrene-ethylene-butylene-styrene (SEBS) polymer.

For some embodiments in which the non-woven material 102 contains polypropylene homopolymer, the first skin layer 6 and/or the second skin layer 8 may contain a blend of about 60% C702-20 and 40% Exceed 3518. In other embodiments, the first skin layer 6 and/or the second skin layer 8 may contain a blend of about 85% 35 MFR polypropylene homopolymer and about 15% of an LDPE, such as Equistar NA334.

For some embodiments in which the non-woven material contains bicomponent polyethylene/polypropylene non-woven material, which is sometimes used for softness, the first skin layer 6 and/or the second skin layer 8 may contain a blend of about 60% C702-20 and about 40% Exceed 3518. In other embodiments, the first skin layer 6 and/or the second skin layer 8 may contain (a) a blend of about 75% Exceed 3518 and about 25% of an LDPE, such as Equistar NA334, or (b) 100% of an HDPE resin.

In illustrative embodiments, a personal hygiene product in accordance with the present disclosure includes at least one stretched elastic film 2 prepared by a process as described above and at least one non-woven layer. The at least one non-woven layer is configured for contacting skin and/or clothing of a user of the personal hygiene product.

In one example, the at least one stretched elastic film is bonded to the at least one non-woven layer without an adhesive (e.g., via heat sealing, ultrasonic welding, and/or the like). In illustrative embodiments, the portion of the stretched elastic film and the portion of the non-woven layer joined via ultrasonic bonding each comprises a common polymer. In some embodiments, the common polymer is polyethylene, polypropylene, or a combination thereof. In illustrative embodiments, the film 2 has a multi-layer structure comprising at least one core film layer 4 interposed between at least a first skin layer 6 and at least a second skin layer 8, and the portion of the stretched elastic film 2 joined to the portion of the non-woven layer via ultrasonic bonding comprises at least a portion of the first skin layer 6.

In some embodiments, each of the at least one stretched elastic film 2 and the at least one non-woven layer comprises polypropylene and/or polyethylene. In illustrative embodiments, each of the at least one stretched elastic film 2 and the at least one non-woven layer comprises polypropylene. In illustrative embodiments, the at least one stretched elastic film is bonded to the at least one outer non-woven layer via an ultrasonic bond.

For embodiments in which the stretched elastic film to be ultrasonically bonded to a nonwoven material is a co-extrusion analogous to that shown in FIG. 1, the outer skin layers of the stretched elastic film 2 may include a material that will ultrasonically bond with the non-woven material. For example, if the stretched elastic film 2 shown in FIG. 1 is a co-extrusion with a target layer ratio of about 7.5/85/7.5, at least the outer 7.5% layers and the non-woven material may include a material such as polypropylene.

In illustrative embodiments, the personal hygiene product in accordance with the present disclosure is configured as an incontinence brief, a surgical gown, or a feminine hygiene product.

The following numbered clauses include embodiments that are contemplated and non-limiting:

Clause 1. A process for making a stretched elastic film comprising the steps of
co-extruding at least a first composition, a second composition, and a third composition to form a molten web.

Clause 2. The process of clause 1, any other suitable clause, or any combination of suitable clauses, wherein the first composition forms at least one first film layer, the second composition forming at least one second film layer, and the third composition forming at least one third film layer.

Clause 3. The process of clause 2, any other suitable clause, or any combination of suitable clauses, wherein the at least one first film layer is disposed between the at least one second film layer and the at least one third film layer.

Clause 4. The process of clause 3, any other suitable clause, or any combination of suitable clauses, wherein the first composition comprises a polyolefin, a styrene block copolymer, a non-styrene block copolymer, or a combination thereof.

Clause 5. The process of clause 4, any other suitable clause, or any combination of suitable clauses, wherein the second composition and the third composition are identical or different.

Clause 6. The process of clause 5, any other suitable clause, or any combination of suitable clauses, further comprising casting the molten web against a surface of a chill roll using an air knife, an air blanket, a vacuum box, or a combination thereof to form a quenched film.

Clause 7. The process of clause 6, any other suitable clause, or any combination of suitable clauses, further comprising stretching the quenched film in a machine direction in at least a 2:1 draw to form the stretched film.

Clause 8. The process of clause 7, any other suitable clause, or any combination of suitable clauses, further comprising relaxing the stretched film to form a relaxed film.

Clause 9. The process of clause 7, any other suitable clause, or any combination of suitable clauses, wherein the polyolefin comprises polyethylene, polypropylene, or a combination thereof.

Clause 10. The process of clause 7, any other suitable clause, or any combination of suitable clauses, wherein the polyolefin comprises low density polyethylene, high density polyethylene, linear low density polyethylene, ultra-low density polyethylene, or a combination thereof.

Clause 11. The process of clause 7, any other suitable clause, or any combination of suitable clauses, wherein the polyolefin comprises linear low density polyethylene.

Clause 12. The process of clause 7, any other suitable clause, or any combination of suitable clauses, wherein the polyolefin comprises linear low density polyethylene and the linear low density polyethylene comprises a metallocene polyethylene.

Clause 13. The process of clause 7, any other suitable clause, or any combination of suitable clauses, wherein the polyolefin comprises polypropylene.

Clause 14. The process of clause 7, any other suitable clause, or any combination of suitable clauses, wherein the polyolefin comprises polypropylene impact copolymer.

Clause 15. The process of clause 7, any other suitable clause, or any combination of suitable clauses, wherein the styrene block copolymer comprises styrene-isoprene block copolymer, styrene-(ethylene-butylene) block copolymer, styrene-(ethylene-propylene) block copolymer, styrene-butadiene block copolymer, or a combination thereof.

Clause 16. The process of clause 7, any other suitable clause, or any combination of suitable clauses, wherein the molten web is cast against the surface of the chill roll under negative pressure by the vacuum box.

Clause 17. The process of clause 7, any other suitable clause, or any combination of suitable clauses, wherein the molten web is cast against the surface of the chill roll under positive pressure by the air knife.

Clause 18. The process of clause 7, any other suitable clause, or any combination of suitable clauses, wherein at least the extruding and the casting are achieved via in-line processing.

Clause 19. The process of clause 7, any other suitable clause, or any combination of suitable clauses, wherein the extruding and the casting are achieved via in-line processing, and wherein the stretching is achieved via post-processing of the quenched film.

Clause 20. The process of clause 7, any other suitable clause, or any combination of suitable clauses, wherein the extruding, the casting, and the stretching are achieved via in-line processing.

Clause 21. The process of clause 7, any other suitable clause, or any combination of suitable clauses, wherein the stretching in the machine direction is in at least a 3:1 draw.

Clause 22. The process of clause 7, any other suitable clause, or any combination of suitable clauses, wherein the stretching in the machine direction is in at least a 4:1 draw.

Clause 23. The process of clause 7, any other suitable clause, or any combination of suitable clauses, wherein at least a portion of the stretching is performed at room temperature.

Clause 24. The process of clause 7, any other suitable clause, or any combination of suitable clauses, wherein the first film layer is a core layer, and wherein each of the at least one second film layer and the at least one third film layer is an outer skin layer.

Clause 25. The process of clause 7, any other suitable clause, or any combination of suitable clauses, wherein each of the second composition and the third composition comprises a polyolefin.

Clause 26. The process of clause 25, any other suitable clause, or any combination of suitable clauses, wherein each of the second composition and the third composition comprises polyethylene, polypropylene, or a combination thereof.

Clause 27. The process of clause 26, any other suitable clause, or any combination of suitable clauses, wherein the second composition and the third composition are identical.

Clause 28. The process of clause 7, any other suitable clause, or any combination of suitable clauses, wherein the stretched elastic film, after relaxation, has a basis weight of less than or equal to about 50 gsm.

Clause 29. The process of clause 7, any other suitable clause, or any combination of suitable clauses, wherein the stretched elastic film, after relaxation, has a basis weight of less than or equal to about 40 gsm.

Clause 30. The process of clause 7, any other suitable clause, or any combination of suitable clauses, wherein the stretched elastic film, after relaxation, has a basis weight of less than or equal to about 30 gsm.

Clause 31. The process of clause 7, any other suitable clause, or any combination of suitable clauses, wherein the stretched elastic film, after relaxation, has a basis weight of less than or equal to about 20 gsm.

Clause 32. The process of clause 7, any other suitable clause, or any combination of suitable clauses, further comprising ageing the quenched film before the stretching to form an aged film, the aged film having an increased elasticity relative to the quenched film.

Clause 33. The process of clause 32, any other suitable clause, or any combination of suitable clauses, wherein the composition comprises a polypropylene copolymer.

Clause 34. A stretched elastic film comprising
an elastomer.

Clause 35. The stretched elastic film of clause 34, any other suitable clause, or any combination of suitable clauses, wherein the stretched elastic film is prepared by a process comprising stretching a quenched film in a machine direction in at least a 2:1 draw to form the stretched film.

Clause 36. The stretched elastic film of clause 35, any other suitable clause, or any combination of suitable clauses, wherein, after relaxation, the stretched elastic film has a load at 100% of less than about 300 grams/inch.

Clause 37. The stretched elastic film of clause 36, any other suitable clause, or any combination of suitable clauses, wherein the elastomer is selected from the group consisting of a polyolefin, a styrene block copolymer, a non-styrene block copolymer, and a combination thereof.

Clause 38. The stretched elastic film of clause 36, any other suitable clause, or any combination of suitable clauses, wherein the process comprises stretching the quenched film in the machine direction in at least a 3:1 draw.

Clause 39. The stretched elastic film of clause 36, any other suitable clause, or any combination of suitable clauses, wherein the process comprises stretching the quenched film in the machine direction in at least a 4:1 draw.

Clause 40 The stretched elastic film of clause 36, any other suitable clause, or any combination of suitable clauses, wherein the film has a multi-layer structure comprising at least one core film layer interposed between at least a first skin layer and at least a second skin layer.

Clause 41. The stretched elastic film of clause 40, any other suitable clause, or any combination of suitable clauses, wherein the multi-layer structure has a layer ratio of about 7.5/85/7.5.

Clause 42. The stretched elastic film of clause 40, any other suitable clause, or any combination of suitable clauses, wherein the multi-layer structure has a layer ratio of about 10/80/10.

Clause 43. The stretched elastic film of clause 40, any other suitable clause, or any combination of suitable clauses, wherein the multi-layer structure has a layer ratio of about 5/90/5.

Clause 44. The stretched elastic film of clause 40, any other suitable clause, or any combination of suitable clauses, wherein the film, after relaxation, has a load at 100% of less than about 250 grams/inch.

Clause 45. The stretched elastic film of clause 40, any other suitable clause, or any combination of suitable clauses, wherein the film, after relaxation, has a load at 100% of less than about 200 grams/inch.

Clause 46. The stretched elastic film of clause 40, any other suitable clause, or any combination of suitable clauses, wherein the film, after relaxation, has a load at 100% of less than about 150 grams/inch.

Clause 47. The stretched elastic film of clause 40, any other suitable clause, or any combination of suitable clauses, wherein the film, after relaxation, has a load at 100% of less than about 125 grams/inch.

Clause 48. The stretched elastic film of clause 40, any other suitable clause, or any combination of suitable clauses, wherein the film, after relaxation, has a basis weight of less than or equal to about 50 gsm.

Clause 49. The stretched elastic film of clause 40, any other suitable clause, or any combination of suitable clauses, wherein the film, after relaxation, has a basis weight of less than or equal to about 40 gsm.

Clause 50. The stretched elastic film of clause 40, any other suitable clause, or any combination of suitable clauses, wherein the film, after relaxation, has a basis weight of less than or equal to about 30 gsm.

Clause 51. A process for making a multi-layer article comprising
attaching at least a portion of the stretched elastic film of clause 34, any other suitable clause, or any combination of suitable clauses, to at least a portion of a non-woven layer via ultrasonic bonding.

Clause 52. The process of clause 51, any other suitable clause, or any combination of suitable clauses, wherein the portion of the stretched elastic film and the portion of the non-woven layer joined via ultrasonic bonding each comprises a common polymer.

Clause 53. The process of clause 52, any other suitable clause, or any combination of suitable clauses, wherein the common polymer is polyethylene, polypropylene, or a combination thereof.

Clause 54. The process of clause 52, any other suitable clause, or any combination of suitable clauses, wherein the common polymer is polypropylene.

Clause 55. The process of clause 52, any other suitable clause, or any combination of suitable clauses, wherein the common polymer is polyethylene.

Clause 56. The process of clause 51, any other suitable clause, or any combination of suitable clauses, wherein the film has a multi-layer structure comprising at least one core film layer interposed between at least a first skin layer and at least a second skin layer, and wherein the portion of the stretched elastic film joined to the portion of the non-woven layer via ultrasonic bonding comprises at least a portion of the first skin layer.

Clause 57. A process for making a personal hygiene product comprising
attaching at least a portion of the stretched elastic film of clause 34, any other suitable clause, or any combination of suitable clauses, to at least a portion of a non-woven layer via ultrasonic bonding to form a personal hygiene product preform.

Clause 58. The process of clause 58, any other suitable clause, or any combination of suitable clauses, applying one or a plurality of additional processing steps to the personal hygiene product preform to form the personal hygiene product.

Clause 59. The process of clause 58, any other suitable clause, or any combination of suitable clauses, wherein the personal hygiene product is configured as a diaper.

Clause 60. The process of clause 58, any other suitable clause, or any combination of suitable clauses, wherein the personal hygiene product is configured as a training pant.

Clause 61. The process of clause 58, any other suitable clause, or any combination of suitable clauses, wherein the personal hygiene product is configured as an incontinence brief.

Clause 62. The process of clause 58, any other suitable clause, or any combination of suitable clauses, wherein the portion of the stretched elastic film and the portion of the non-woven layer joined via ultrasonic bonding each comprises a common polymer.

Clause 63. The process of clause 62, any other suitable clause, or any combination of suitable clauses, wherein the common polymer is polyethylene, polypropylene, or a combination thereof.

Clause 64. The process of clause 62, any other suitable clause, or any combination of suitable clauses, wherein the common polymer is polypropylene.

Clause 65. The process of clause 62, any other suitable clause, or any combination of suitable clauses, wherein the common polymer is polyethylene.

Clause 66. The process of clause 58, any other suitable clause, or any combination of suitable clauses, wherein the film has a multi-layer structure comprising at least one core film layer interposed between at least a first skin layer and at least a second skin layer, and wherein the portion of the stretched elastic film joined to the portion of the non-woven layer via ultrasonic bonding comprises at least a portion of the first skin layer.

Clause 67. The process of clause 58, any other suitable clause, or any combination of suitable clauses, further comprising cutting the stretched elastic film into two or more segments, placing the two or more segments at intermittent positions on the nonwoven layer, and applying ultrasonic bonding at the intermittent positions.

Clause 68. The process of clause 67, any other suitable clause, or any combination of suitable clauses, wherein the personal hygiene product is configured as a training pant.

Clause 69. The process of clause 58, any other suitable clause, or any combination of suitable clauses, wherein the personal hygiene product is configured as a diaper, a training pant, or an incontinence brief.

Clause 70. The process of clause 69, any other suitable clause, or any combination of suitable clauses, further comprising applying the stretched elastic film to at least a first portion and a second portion of the non-woven layer, wherein the first portion and the second portion correspond, respectively, to a first leg-hole and a second leg hole, and applying ultrasonic bonding to at least a portion of each of the first portion and the second portion.

Clause 71. The process of clause 58, any other suitable clause, or any combination of suitable clauses, wherein the one or the plurality of additional processing steps comprise cutting, gluing, ultrasonically bonding, heating, cooling, thermal welding, folding, printing, or a combination thereof.

Clause 72. A personal hygiene product comprising
the stretched elastic film of clause 34, any other suitable clause, or any combination of suitable clauses, and
a nonwoven layer.

Clause 73. The personal hygiene product of clause 72, any other suitable clause, or any combination of suitable clauses, wherein at least a portion of the stretched elastic film is ultrasonically bonded to at least a portion of the non-woven layer.

Clause 74. The personal hygiene product of clause 73, any other suitable clause, or any combination of suitable clauses, wherein the stretched elastic film has a multi-layer structure comprising at least one core film layer interposed between at least a first skin layer and at least a second skin layer, and wherein the portion of the stretched elastic film joined to the portion of the non-woven layer via ultrasonic bonding comprises at least a portion of the first skin layer.

Clause 75. The personal hygiene product of clause 73, any other suitable clause, or any combination of suitable clauses, wherein the stretched elastic film comprises two or more non-continuous segments attached to different portions of the nonwoven layer.

Clause 76. The personal hygiene product of clause 75, any other suitable clause, or any combination of suitable clauses, wherein the two or more non-continuous segments are positioned along a waistband portion of a pants-type article.

Clause 77. The personal hygiene product of clause 76, any other suitable clause, or any combination of suitable clauses, wherein the pants-type article is a diaper, a training pant, or an incontinence brief.

Clause 78. The personal hygiene product of clause 73, any other suitable clause, or any combination of suitable clauses, wherein the stretched elastic film is attached to at least a first portion and a second portion of the personal hygiene product, wherein the first portion and the second portion correspond, respectively, to a first leg-hole and a second leg hole of a pants-type article.

Clause 79. The personal hygiene product of clause 78, any other suitable clause, or any combination of suitable clauses, wherein the pants-type article is a diaper, a training pant, or an incontinence brief.

Clause 80. The personal hygiene product of clause 73, any other suitable clause, or any combination of suitable clauses, wherein the stretched elastic film is bonded to the non-woven layer without an adhesive.

Clause 81. The personal hygiene product of clause 73, any other suitable clause, or any combination of suitable clauses, wherein each of the stretched elastic film and the non-woven layer comprises polypropylene.

Clause 82. The personal hygiene product of clause 73, any other suitable clause, or any combination of suitable clauses, wherein each of the stretched elastic film and the non-woven layer comprises polyethylene.

The following examples and representative procedures illustrate features in accordance with the present disclosure, and are provided solely by way of illustration. They are not intended to limit the scope of the appended claims or their equivalents.

EXAMPLES

General

For production of the example films, an extrusion cast line with up to 3 extruders was used. The "A" and "B" extruders are 2½" in diameter, and the "C" extruder is 1¾" in diameter. The extruders feed into a combining feedblock manufactured by Cloeren Corporation of Orange, Tex., which can layer the A, B and C extruder outputs in a variety of configurations. From the feedblock, the molten polymer proceeds into a monolayer cast die (manufactured by Cloeren) that is about 36" wide. The die has an adjustable gap. For the samples described herein, the adjustable gap was maintained between 10 and 40 mils. The molten polymer drops down to a chill roll. For the samples described herein, the chill roll had an embossed pattern FST-250 which was engraved by Pamarco of Roselle, N.J. as their pattern P-2739. The embossed pattern P-2739 is a square pattern (e.g., with lines nearly aligned with the Machine Direction) with 250 squares per inch and a depth of about 31 microns. The roll itself has an 18" diameter with internal water cooling. The engrave roll pattern may be replaced with other patterns that are shallow enough not to interfere with a vacuum box quench. One alternative is a 40 Ra pattern (40 micro-inch average roughness) generated by a sand-blasting process on a chrome plated roll.

Example 1—Polypropylene-Based Elastic Films

In this experiment, elastic films were made from the formulation XC3-828-2358.0-a shown in Table 1, the formulation XC3-828-2358.1 shown in Table 2, the formulation XC3-828-2358.5 shown in Table 3, and the formulation XC3-828-2358.6 shown in Table 4.

TABLE 1

| | | Composition of XC3-828-2358.0-a. | |
| --- | --- | --- | --- |
| EXTRUDER | Layer % (Total) | COMPONENT | Amount of Component (Weight %) |
| B | 85.0 | INFUSE ™ 9107 (Dow Chemical Company, olefin block copolymer | 100 |
| C (split) | 7.5/7.5 | CP360 (Braskem, homopolymer polypropylene, narrow MWD) | 60 |
| | | PETROTHENE ® NA334000 (LyondellBasell, low density polyethylene) | 40 |

TABLE 2

| | | Composition of XC3-828-2358.1. | |
| --- | --- | --- | --- |
| EXTRUDER | Layer % (Total) | COMPONENT | Amount of Component (Weight %) |
| B | 85.0 | INFUSE ™ 9507 (Dow Chemical Company, olefin block copolymer) | 100 |
| C (split) | 7.5/7.5 | C702-20 (Braskem, impact copolymer polypropylene) | 60 |
| | | EXCEED LL3518 (ExxonMobil, metallocene polyethylene resin, narrow MWD, density = 0.918 g/cm$^3$) | 40 |

TABLE 3

Composition of XC3-828-2358.5.

| EXTRUDER | Layer % (Total) | COMPONENT | Amount of Component (Weight %) |
|---|---|---|---|
| B | 85.0 | VISTAMAXX ™ 6102 (ExxonMobil, propylene-based elastomer | 100 |
| C (split) | 7.5/7.5 | C702-20 (Braskem, impact copolymer polypropylene) | 60 |
|  |  | EXCEED LL3518 (ExxonMobil, metallocene polyethylene resin, narrow MWD, density = 0.918 g/cm$^3$) | 40 |

TABLE 4

Composition of XC3-828-2358.6.

| EXTRUDER | Layer % (Total) | COMPONENT | Amount of Component (Weight %) |
|---|---|---|---|
| B | 85.0 | VISTAMAXX ™ 6102 (ExxonMobil, propylene-based elastomer | 91.70 |
|  |  | C702-20 (Braskem, Impact Copolymer Polypropylene) | 5.00 |
|  |  | EXCEED LL3518 (ExxonMobil, metallocene polyethylene resin, narrow MWD, density = 0.918 g/cm$^3$) | 3.30 |
| C (split) | 7.5/7.5 | C702-20 (Braskem, Impact Copolymer Polypropylene) | 60 |
|  |  | EXCEED LL3518 (ExxonMobil, metallocene polyethylene resin, narrow MWD, density = 0.918 g/cm$^3$) | 40 |

Example 2—Notched Tensile Test Data

Tensile strength of notched films prepared from the formulation XC3-828-2358.0-a shown in Table 1, the formulation XC3-828-2358.1 shown in Table 2, the formulation XC3-828-2358.5 shown in Table 3, and the formulation XC3-828-2358.6 shown in Table 4 were evaluated using the Standard Tensile Test (ASTM D882). A rectangular sample one-inch wide was placed in Tensile tester grips that were two inches apart. A one-eighth-inch notch was made at the midpoint on one side of each of the film samples. In the test, the upper jaw moves at 20 inches per minute and proceeds until the sample breaks.

The tensile test data for films prepared from formulation XC3-828-2358.0-a are summarized in Table 5 below.

The tensile test data for films prepared from formulation XC3-828-2358.1 are summarized in Table 6 below.

The tensile test data for films prepared from formulation XC3-828-2358.5 are summarized in Table 7 below.

The tensile test data for films prepared from formulation XC3-828-2358.6 are summarized in Table 8 below.

TABLE 5

Tensile test data for films prepared from formulation XC3-828-2358.0-a.

| Properties | Elong. % | MD Tensile Std. | Elong. % | MD Tensile Notched | Elong. % | Prestretch MD Tensile | Elong. % | Prestretched MD Tensile Notched |
|---|---|---|---|---|---|---|---|---|
| Gauge |  | 1.38 |  | 1.39 |  | 1.38 |  | 1.38 |
| Gauge (mils) |  | 1.38 |  | 1.39 |  | 1.38 |  | 1.38 |
| MD5 | 5 | 762 | 5 | 102 | 5 | 661 | 5 | 29 |
| MD10 | 10 | 780 | 10 | 252 | 10 | 768 | 10 | 62 |
| MD25 | 25 | 840 | 25 | 301 | 25 | 1026 | 25 | 111 |
| MD50 | 50 | 954 | 50 | 311 | 50 | 1451 | 50 | 163 |
| MD100 | 100 | 1231 | 100 | 270 | 100 | 2594 | 100 | 336 |
| Force at Peak (grams/inch) | 350 | 3204 | 57 | 312 | 131 | 3326 | 96 | 344 |
| Force at Break (grams/inch) | 351 | 3193 | 91 | 282 | 131 | 3313 | 105 | 314 |
| Total Energy Absorbed (ft-lb/in$^2$) |  | 2165 |  | 69 |  | 706 |  | 53 |

| REDUCTION BY NOTCH | No Prestretch | Prestretch |
|---|---|---|
| Peak Elongation | 84% | 27% |
| Break Elongation | 74% | 20% |
| Total Energy | 97% | 92% |

TABLE 6

Tensile test data for films prepared from formulation XC3-828-2358.1.

| Properties | Elong. % | MD Tensile Std. | Elong. % | MD Tensile Notched | Elong. % | Prestretch MD Tensile | Elong. % | Prestretched MD Tensile Notched |
|---|---|---|---|---|---|---|---|---|
| Gauge (mils) | | 1.35 | | 1.35 | | 1.35 | | 1.35 |
| MD5 | 5 | 309 | 5 | 134 | 5 | 160 | 5 | 23 |
| MD10 | 10 | 312 | 10 | 188 | 10 | 190 | 10 | 44 |
| MD25 | 25 | 324 | 25 | 237 | 25 | 290 | 25 | 75 |
| MD50 | 50 | 346 | 50 | 247 | 50 | 446 | 50 | 108 |
| MD100 | 100 | 401 | 100 | 255 | 100 | 818 | 100 | |
| Force at Peak (grams/inch) | 519 | 1343 | 159 | 277 | 154 | 1174 | 96 | 242 |
| Force at Break (grams/inch) | 520 | 1237 | 184 | 251 | 154 | 1174 | 101 | 238 |
| Total Energy Absorbed (ft-lb/in$^2$) | | 1197 | | 124 | | 290 | | 35 |

| REDUCTION BY NOTCH | No Prestretch | Prestretch |
|---|---|---|
| Peak Elongation | 69% | 38% |
| Break Elongation | 65% | 34% |
| Total Energy | 90% | 88% |

TABLE 7

Tensile test data for films prepared from formulation XC3-828-2358.5.

| Properties | Elong. % | MD Tensile Std. | Elong. % | MD Tensile Notched | Elong. % | Prestretch MD Tensile | Elong. % | Prestretched MD Tensile Notched |
|---|---|---|---|---|---|---|---|---|
| Gauge (mils) | | 1.3 | | 1.3 | | 1.3 | | 1.3 |
| MD5 | 5 | 805 | 5 | 125 | 5 | 800 | 5 | 29 |
| MD10 | 10 | 823 | 10 | 187 | 10 | 890 | 10 | 59 |
| MD25 | 25 | 876 | 25 | 258 | 25 | 1104 | 25 | 99 |
| MD50 | 50 | 978 | 50 | 282 | 50 | 1448 | 50 | 139 |
| MD100 | 100 | 1228 | 100 | 247 | 100 | 2360 | 100 | 248 |
| Force at Peak (grams/inch) | 302 | 2801 | 78 | 292 | 132 | 3088 | 93 | 264 |
| Force at Break (grams/inch) | 302 | 2801 | 99 | 269 | 133 | 2968 | 102 | 239 |
| Total Energy Absorbed (ft-lb/in$^2$) | | 1850 | | 72 | | 758 | | 43 |

| REDUCTION BY NOTCH | No Prestretch | Prestretch |
|---|---|---|
| Peak Elongation | 74% | 30% |
| Break Elongation | 67% | 23% |
| Total Energy | 96% | 94% |

TABLE 8

Tensile test data for films prepared from formulation XC3-828-2358.6.

| Properties | Elong. % | MD Tensile Std. | Elong. % | MD Tensile Notched | Elong. % | Prestretch MD Tensile | Elong. % | Prestretched MD Tensile Notched |
|---|---|---|---|---|---|---|---|---|
| Gauge (mils) | | 1.35 | | 1.35 | | 1.35 | | 1.35 |
| MD5 | 5 | 1200 | 5 | 179 | 5 | 961 | 5 | 38 |
| MD10 | 10 | 1230 | 10 | 258 | 10 | 1113 | 10 | 77 |
| MD25 | 25 | 1332 | 25 | 359 | 25 | 1586 | 25 | 147 |

TABLE 8-continued

Tensile test data for films prepared from formulation XC3-828-2358.6.

| Properties | Elong. % | MD Tensile Std. | Elong. % | MD Tensile Notched | Elong. % | Prestretch MD Tensile | Elong. % | Prestretched MD Tensile Notched |
|---|---|---|---|---|---|---|---|---|
| MD50 | 50 | 1524 | 50 | 404 | 50 | 2278 | 50 | 241 |
| MD100 | 100 | 1981 | 100 | 245 | 100 | | 100 | |
| Force at Peak (grams/inch) | 224 | 3777 | 59 | 407 | 107 | 4517 | 79 | 369 |
| Force at Break (grams/inch) | 224 | 3777 | 59 | 369 | 107 | 4363 | 88 | 334 |
| Total Energy Absorbed (ft-lb/in$^2$) | | 1986 | | 77 | | 827 | | 52 |

| REDUCTION BY NOTCH | No Prestretch | Prestretch |
|---|---|---|
| Peak Elongation | 74% | 26% |
| Break Elongation | 74% | 18% |
| Total Energy | 96% | 94% |

The physical properties of the resultant films prepared from formulations XC3-828-2358.0-a, XC3-828-2358.1, XC3-828-2358.5, and XC3-828-2358.6 are shown in Table 9 below. All of the films had a 7.5/85/7.5 A/B/A layering.

TABLE 9

Physical Properties of Elastic Films Prepared from Formulations XC3-828-2358.0-a, XC3-828-2358.1, XC3-828-2358.5, and XC3-828-2358.6.

| Properties | Units | XC3-828-2358.0-a | XC3-828-2358.1 | XC3-828-2358.5 | XC3-828-2358.6 |
|---|---|---|---|---|---|
| Basis Weight | g/m$^2$ | 30 | 30 | 29 | 29 |
| Tensile Gauge MD | mil | 1.34 | 1.39 | 1.26 | 1.37 |
| Force @ Peak MD | g/in | 3,573 | 1,318 | 2,467 | 4,171 |
| Strain @ Peak MD | % | 776 | 679 | 649 | 626 |
| Force @ Break MD | g/in | 3,566 | 1,315 | 2,464 | 4,166 |
| Strain @ Break MD | % | 776 | 679 | 649 | 626 |
| Force @ Yield MD | g/in | 241 | 234 | 175 | 237 |
| Strain @ Yield MD | % | 11 | 16 | 11 | 11 |
| Force @ 5% Strain MD | g/in | 152 | 122 | 95 | 130 |
| Force @ 10% Strain MD | g/in | 231 | 193 | 165 | 228 |
| Force @ 25% Strain MD | g/in | 296 | 258 | 243 | 338 |
| Force @ 50% Strain MD | g/in | 312 | 265 | 268 | 393 |
| Force @ 100% Strain MD | g/in | 336 | 274 | 295 | 441 |
| TEA MD | FtLb/in$^2$ | 2,561 | 1,095 | 1,640 | 2,284 |
| Elmendorf Tear MD Arm | g | 400 | 200 | 200 | 200 |
| ††††Elmendorf Tear MD | gf | 161 | 135 | 152 | 110 |
| Tensile Gauge TD | mil | 1.36 | 1.33 | 1.30 | 1.29 |
| Force @ Peak TD | g/in | 815 | 503 | 2,148 | 2,050 |
| Strain @ Peak TD | % | 818 | 757 | 994 | 957 |
| Force @ Break TD | g/in | 815 | 503 | 2,148 | 2,048 |
| Strain @ Break TD | % | 817 | 759 | 994 | 957 |
| Force @ Yield TD | g/in | 269 | 192 | 190 | 249 |
| Strain @ Yield TD | % | 18 | 19 | 15 | 17 |
| Force @ 5% Strain TD | g/in | 151 | 99 | 97 | 116 |
| Force @ 10% Strain TD | g/in | 231 | 161 | 158 | 199 |
| Force @ 25% Strain TD | g/in | 277 | 197 | 220 | 276 |
| Force @ 50% Strain TD | g/in | 280 | 202 | 242 | 296 |
| Force @ 100% Strain TD | g/in | 280 | 206 | 253 | 303 |
| TEA TD | FtLb/in$^2$ | 995 | 636 | 1,993 | 2,045 |
| Elmendorf Tear TD Arm | g | 1,600 | 800 | 800 | 800 |
| Elmendorf Tear TD | gf | 458 | 306 | 200 | 265 |
| § Slow Puncture - ¼" (D3) | gf | 1,071 | 864 | 973 | — |
| § Slow Puncture - ⅛" | gf | 535 | | | |
| CD 100% Hysteresis | | | | | |
| 1st Cycle Load at Peak | gf | 290 | 216 | 399 | 339 |
| 1st Cycle Load at 50% | gf | 288 | 213 | 377 | 334 |
| 1st Cycle Unload at 50% | gf | 22 | 18 | 42 | 45 |
| Extension Set, second load | inches | 0.253 | 0.259 | 0.089 | 0.156 |
| | % | 12.65 | 12.95 | 4.45 | 7.8 |
| second unload | inches | 0.492 | 0.515 | 0.383 | 0.377 |
| | % | 24.6 | 25.75 | 19.15 | 18.85 |

Films prepared from the formulations XC3-828-2358.0-a, XC3-828-2358.1, XC3-828-2358.5, and XC3-828-2358.6 were subjected to machine direction pre-stretching. The MD 100% hysteresis testing data are summarized in Table 10 below.

TABLE 10

MD 100% Hysteresis Testing Data For Films After MD Stretching.

| Prestretch - From 1" to 4" | Units | XC3-828-2358.0-a | XC3-828-2358.1 | XC3-828-2358.5 | XC3-828-2358.6 |
|---|---|---|---|---|---|
| Final Length MD 100% Hysteresis | inches | 1.9375 | 1.708 | 1.5625 | 1.79 |
| 1st Cycle Load at Peak | gf | 402 | 132 | 178 | 422 |
| 1st Cycle Load at 50% | gf | 212 | 84 | 115 | 191 |
| 1st Cycle Unload at 50% | gf | 56 | 26 | 46 | 53 |
| Extension Set, second load | inches | 0.097 | 0.063 | 0.126 | 0.083 |
|  | % | 4.85 | 3.15 | 6.3 | 4.15 |
| second unload | inches | 0.327 | 0.424 | 0.259 | 0.262 |
|  | % | 16.35 | 21.2 | 12.95 | 13.1 |

The MD 100% Hysteresis testing data for the films prepared from the formulations XC3-828-2358.0-a, XC3-828-2358.1, XC3-828-2358.5, and XC3-828-2358.6 that were not subjected to machine direction pre-stretching are summarized in Table 11 below.

TABLE 11

MD 100% Hysteresis Testing Data For Films Without MD Stretching.

| MD 100% Hysteresis | Units | XC3-828-2358.0-a | XC3-828-2358.1 | XC3-828-2358.5 | XC3-828-2358.6 |
|---|---|---|---|---|---|
| 1st Cycle Load at Peak | gf | 367 | 274 | 359 | 490 |
| 1st Cycle Load at 50% | gf | 345 | 267 | 327 | 436 |
| 1st Cycle Unload at 50% | gf | 47 | 25 | 49 | 61 |
| Extension Set, second load | inches | 0.196 | 0.216 | 0.149 | 0.133 |
|  | % | 9.8 | 10.8 | 7.45 | 6.65 |
| second unload | inches | 0.375 | 0.465 | 0.36 | 0.337 |
|  | % | 18.75 | 23.25 | 18 | 16.85 |

Example 3—Polypropylene-Based Elastic Films

In this experiment, elastic films were made from the formulation XC3-828-2358.0 shown in Table 12, the formulation XC3-888-2376.0 shown in Table 13, the formulation XC3-888-2376.0 shown in Table 14, the formulation XC3-898-2407.0 shown in Table 15, the formulation XC3-888-2405.0 shown in Table 16, the formulation XC3-888-2408.0 shown in Table 17, the formulation XC3-888-2408.1 shown in Table 18, the formulation XC3-888-2405.1 shown in Table 19, the formulation XC3-888-2405.2 shown in Table 20, and the formulation XC3-888-2405.3 shown in Table 21.

TABLE 12

Composition of XC3-828-2358.0.

| EXTRUDER | Layer % (Total) | COMPONENT | Amount of Component (Weight %) |
|---|---|---|---|
| B | 85.0 | INFUSE ™ 9107 (Dow Chemical Company, olefin block copolymer | 100 |
| C (split) | 7.5/7.5 | C702-20 (Braskem, impact copolymer polypropylene) | 60 |
|  |  | EXCEED LL3518 (ExxonMobil, metallocene polyethylene resin, narrow MWD, density = 0.918 g/cm$^3$) | 40 |

TABLE 13

Composition of XC3-888-2376.0.

| EXTRUDER | Layer % (Total) | COMPONENT | Amount of Component (Weight %) |
|---|---|---|---|
| B | 85.0 | VISTAMAXX ™ 6102 (ExxonMobil, propylene-based elastomer | 100 |
| C (split) | 7.5/7.5 | C702-20 (Braskem, impact copolymer polypropylene) | 60 |
|  |  | EXCEED LL3518 (ExxonMobil, metallocene polyethylene resin, narrow MWD, density = 0.918 g/cm$^3$) | 40 |

TABLE 14

Composition of XC3-898-2407.0.

| EXTRUDER | Layer % (Total) | COMPONENT | Amount of Component (Weight %) |
|---|---|---|---|
| B | 85.0 | LC478-139 (PolyOne, styrenic block copolymer compound) | 100 |
| C (split) | 7.5/7.5 | C702-20 (Braskem, impact copolymer polypropylene) | 60 |
|  |  | EXCEED LL3518 (ExxonMobil, metallocene polyethylene resin, narrow MWD, density = 0.918 g/cm$^3$) | 30 |
|  |  | 111017P White PE MB (Ampacet, white masterbatch LLD polyethylene) | 10 |

TABLE 15

Composition of XC3-888-2405.0.

| EXTRUDER | Layer % (Total) | COMPONENT | Amount of Component (Weight %) |
|---|---|---|---|
| B | 85.0 | VISTAMAXX ™ 6102 (ExxonMobil, propylene-based elastomer | 60 |
|   |   | F4901 (Kuraray America Inc., SEEPS) | 40 |
| C (split) | 7.5/7.5 | C702-20 (Braskem, impact copolymer polypropylene) | 60 |
|   |   | EXCEED LL3518 (ExxonMobil, metallocene polyethylene resin, narrow MWD, density = 0.918 g/cm$^3$) | 40 |

TABLE 16

Composition of XC3-888-2408.0.

| EXTRUDER | Layer % (Total) | COMPONENT | Amount of Component (Weight %) |
|---|---|---|---|
| B | 85.0 | VISTAMAXX ™ 6102 (ExxonMobil, propylene-based elastomer | 60 |
|   |   | YT021 (Kuraray America Inc., SEEPS) | 40 |
| C (split) | 7.5/7.5 | C702-20 (Braskem, impact copolymer polypropylene) | 60 |
|   |   | EXCEED LL3518 (ExxonMobil, metallocene polyethylene resin, narrow MWD, density = 0.918 g/cm$^3$) | 40 |

TABLE 17

Composition of XC3-888-2408.1.

| EXTRUDER | Layer % (Total) | COMPONENT | Amount of Component (Weight %) |
|---|---|---|---|
| B | 85.0 | VISTAMAXX ™ 6102 (ExxonMobil, propylene-based elastomer | 60 |
|   |   | YT022 (Kuraray America Inc., SEEPS) | 40 |
| C (split) | 7.5/7.5 | C702-20 (Braskem, impact copolymer polypropylene) | 60 |
|   |   | EXCEED LL3518 (ExxonMobil, metallocene polyethylene resin, narrow MWD, density = 0.918 g/cm$^3$) | 40 |

TABLE 18

Composition of XC3-888-2405.1.

| EXTRUDER | Layer % (Total) | COMPONENT | Amount of Component (Weight %) |
|---|---|---|---|
| B | 85.0 | VISTAMAXX ™ 6102 (ExxonMobil, propylene-based elastomer | 60 |
|   |   | F4901 (Kuraray America Inc., SEEPS) | 40 |
| C (split) | 7.5/7.5 | C702-20 (Braskem, impact copolymer polypropylene) | 60 |
|   |   | EXCEED LL3518 (ExxonMobil, metallocene polyethylene resin, narrow MWD, density = 0.918 g/cm$^3$) | 36 |
|   |   | 101736 (Ampacet Corporation, 20 wt. % masterbatch of 50 wt. % diatomaceous earth in LDPE) | 4 |

TABLE 19

Composition of XC3-888-2405.2.

| EXTRUDER | Layer % (Total) | COMPONENT | Amount of Component (Weight %) |
|---|---|---|---|
| B | 85.0 | VISTAMAXX ™ 6102 (ExxonMobil, propylene-based elastomer | 60 |
|   |   | F4901 (Kuraray America Inc., SEEPS) | 40 |
| C (split) | 7.5/7.5 | C702-20 (Braskem, impact copolymer polypropylene) | 60 |
|   |   | EXCEED LL3518 (ExxonMobil, metallocene polyethylene resin, narrow MWD, density = 0.918 g/cm$^3$) | 33 |
|   |   | 101736 (Ampacet Corporation, 20 wt. % masterbatch of 50 wt. % diatomaceous earth in LDPE) | 4 |
|   |   | 101797 (Ampacet Corporation, oleamide) | 3 |

TABLE 20

Composition of XC3-888-2405.3.

| EXTRUDER | Layer % (Total) | COMPONENT | Amount of Component (Weight %) |
|---|---|---|---|
| B | 85.0 | VISTAMAXX ™ 6102 (ExxonMobil, propylene-based elastomer | 60 |
| | | F4901 (Kuraray America Inc., SEEPS) | 40 |
| C (split) | 7.5/7.5 | C702-20 (Braskem, impact copolymer polypropylene) | 60 |
| | | EXCEED LL3518 (ExxonMobil, metallocene polyethylene resin, narrow MWD, density = 0.918 g/cm³) | 33 |
| | | 101736 (Ampacet Corporation, 20 wt. % masterbatch of 50 wt. % diatomaceous earth in LDPE) | 4 |
| | | 10433 (Ampacet Corporation, bisstearamide) | 3 |

The physical properties of the resultant films prepared from formulations XC3-828-2358.0, XC3-888-2376.0, XC3-898-2407.0, XC3-888-2405.0, XC3-888-2408.0, XC3-888-2408.1, XC3-888-2405.1, XC3-888-2405.2, XC3-888-2405.3, and XC3-888-2405.0 (High Temp.) are shown in Tables 21-23 below. All of the films had a 7.5/85/7.5 A/B/A layering.

TABLE 21

Physical Properties of Elastic Films Prepared from Formulations XC3-828-2358.0 and XC3-888-2376.0.

| Properties | Units | XC3-828-2358.0 | XC3-828-2358.0 | XC3-888-2376.0 | XC3-888-2376.0 |
|---|---|---|---|---|---|
| Basis Weight | g/m² | 30 | 30 | 30 | 31 |
| Light Transmission | % | | | | |
| Tensile Gauge MD | mil | 1.4 | 1.31 | 1.35 | 1.36 |
| Force @ Peak MD | g/in | 3446 | 3089 | 2815 | 2658 |
| Strain @ Peak MD | % | 623 | 569 | 744 | 730 |
| Force @ Break MD | g/in | 3445 | 3089 | 2815 | 2658 |
| Strain @ Break MD | % | 624 | 569 | 744 | 730 |
| Force @ Yield MD | g/in | 302 | 306 | 289 | 273 |
| Strain @ Yield MD | % | 17 | 18 | 22 | 18 |
| Force @ 5% Strain MD | g/in | 175 | 174 | 148 | 161 |
| Force @ 10% Strain MD | g/in | 256 | 255 | 226 | 226 |
| Force @ 25% Strain MD | g/in | 322 | 322 | 296 | 290 |
| Force @ 50% Strain MD | g/in | 338 | 340 | 320 | 312 |
| Force @ 100% Strain MD | g/in | 370 | 376 | 346 | 337 |
| TEA MD | FtLb/in² | 4 | 4 | 4 | 4 |
| Elmendorf Tear MD Arm | g | 200 | 200 | 200 | 200 |
| Elmendorf Tear MD | gf | 117 | 91 | 147 | 139 |
| Tensile Gauge TD | mil | 1.33 | 1.32 | 1.33 | 1.35 |
| Force @ Peak TD | g/in | 788 | 719 | 2025 | 2062 |
| Strain @ Peak TD | % | 828 | 776 | 948 | 941 |
| Force @ Break TD | g/in | 767 | 697 | 2025 | 2062 |
| Strain @ Break TD | % | 867 | 825 | 948 | 941 |
| Force @ Yield TD | g/in | 259 | 252 | 239 | 264 |
| Strain @ Yield TD | % | 17 | 19 | 18 | 18 |
| Force @ 5% Strain TD | g/in | 174 | 167 | 130 | 153 |
| Force @ 10% Strain TD | g/in | 233 | 224 | 194 | 219 |
| Force @ 25% Strain TD | g/in | 264 | 255 | 255 | 280 |
| Force @ 50% Strain TD | g/in | 262 | 255 | 273 | 296 |
| Force @ 100% Strain TD | g/in | 264 | 257 | 286 | 305 |
| TEA TD | FtLb/in² | 2 | 2 | 4 | 4 |
| Elmendorf Tear TD Arm | g | 800 | 800 | 200 | 200 |
| Elmendorf Tear TD | gf | 362 | 400 | 147 | 152 |
| 100% MD Hysteresis | | No Prestretch | No Prestretch | No Prestretch | No Prestretch |
| 1st Cycle | | | | | |
| Load @25% | g/inch | 327 | 357 | 313 | 320 |
| Load @50% | g/inch | 343 | 374 | 335 | 341 |
| Load @75% | g/inch | 356 | 388 | 346 | 352 |
| Load @100% | g/inch | 372 | 404 | 357 | 363 |

TABLE 21-continued

Physical Properties of Elastic Films Prepared from Formulations XC3-828-2358.0 and XC3-888-2376.0.

| Properties | Units | XC3-828-2358.0 | XC3-828-2358.0 | XC3-888-2376.0 | XC3-888-2376.0 |
|---|---|---|---|---|---|
| −30 second delay | | | | | |
| Unload @100% | g/inch | 196 | 226 | 179 | 187 |
| Unload @75% | g/inch | 105 | 111 | 95 | 96 |
| Unload @50% | g/inch | 50 | 51 | 41 | 41 |
| Unload @25% | g/inch | −1 | 0 | 1 | 1 |
| −60 second delay 2nd Cycle | | | | | |
| Load @25% | g/inch | 129 | 138 | 83 | 88 |
| Load @50% | g/inch | 218 | 236 | 196 | 200 |
| Load @75% | g/inch | 278 | 303 | 260 | 265 |
| Load @100% | g/inch | 346 | 380 | 330 | 335 |
| −30 second delay | | | | | |
| Unload @100% | g/inch | 180 | 211 | 165 | 177 |
| Unload @75% | g/inch | 105 | 112 | 96 | 97 |
| Unload @50% | g/inch | 47 | 50 | 38 | 39 |
| Unload @25% | g/inch | −1 | 0 | 1 | 1 |
| Length after Pre-stretching (started at 1") | | 1.72 | 1.72 | 1.67 | 1.67 |

| 100% MD Hysteresis | | Prestretched 4:1 | Prestretched 4:1 | Prestretched 4:1 | Prestretched 4:1 |
|---|---|---|---|---|---|
| 1st Cycle | | | | | |
| Load @25% | g/inch | 98 | 89 | 84 | 95 |
| Load @50% | g/inch | 137 | 132 | 120 | 133 |
| Load @75% | g/inch | 164 | 158 | 148 | 165 |
| Load @100% | g/inch | 216 | 196 | 183 | 211 |
| −30 second delay | | | | | |
| Unload @100% | g/inch | 105 | 98 | 90 | 95 |
| Unload @75% | g/inch | 63 | 60 | 63 | 69 |
| Unload @50% | g/inch | 36 | 33 | 39 | 45 |
| Unload @25% | g/inch | 5 | 2 | 11 | 17 |
| −60 second delay 2nd Cycle | | | | | |
| Load @25% | g/inch | 70 | 61 | 61 | 70 |
| Load @50% | g/inch | 113 | 107 | 98 | 108 |
| Load @75% | g/inch | 143 | 137 | 126 | 139 |
| Load @100% | g/inch | 208 | 189 | 172 | 198 |
| −30 second delay | | | | | |
| Unload @100% | g/inch | 92 | 82 | 74 | 78 |
| Unload @75% | g/inch | 63 | 59 | 63 | 69 |
| Unload @50% | g/inch | 34 | 31 | 40 | 44 |
| Unload @25% | g/inch | 2 | 1 | 11 | 16 |

| | | Sample | | | |
|---|---|---|---|---|---|
| | | A | B | C | D |
| 50% Stretch | 5 minutes | 9 | 8.875 | 9.375 | 9.375 |
| Creep Length | 1 hour | 8.625 | 8.5 | 9.125 | 9.125 |
| 100% Stretch | 5 minutes | 8.531 | 8.5 | 9.0625 | 9.937 |
| Creep Length | 1 hour | 8 | 8.0625 | 8.6875 | 8.625 |

TABLE 22

Physical Properties of Elastic Films Prepared from Formulations XC3-898-2407.0, XC3-888-2405.0, XC3-888-2408.0, and XC3-888-2408.1.

| Properties | Units | XC3-898-2407.0 | XC3-888-2405.0 | XC3-888-2408.0 | XC3-888-2408.1 |
|---|---|---|---|---|---|
| Basis Weight | g/m² | 28.8 | 28 | 30 | 28 |
| Light Transmission | % | 70.7 | | | |
| Tensile Gauge MD | mil | 1.31 | 1.41 | 1.37 | 1.36 |
| Force @ Peak MD | g/in | 2007 | 2,304 | 2,611 | 2,165 |
| Strain @ Peak MD | % | 666 | 680 | 579 | 611 |
| Force @ Break MD | g/in | 2007 | 2,300 | 2,609 | 2,165 |
| Strain @ Break MD | % | 666 | 685 | 581 | 612 |
| Force @ Yield MD | g/in | 262 | 1,772 | 2,481 | 1,928 |
| Strain @ Yield MD | % | 17 | 531 | 554 | 556 |
| Force @ 5% Strain MD | g/in | 174 | 143 | 180 | 154 |
| Force @ 10% Strain MD | g/in | 229 | 211 | 253 | 230 |
| Force @ 25% Strain MD | g/in | 278 | 278 | 316 | 305 |
| Force @ 50% Strain MD | g/in | 298 | 299 | 331 | 325 |
| Force @ 100% Strain MD | g/in | 327 | 318 | 352 | 343 |
| TEA MD | FtLb/in² | 3.4 | 3.7 | 3.1 | 3 |
| Elmendorf Tear MD Arm | g | 400 | 200 | 200 | 200 |
| Elmendorf Tear MD | gf | 149 | 118 | 106 | 70 |
| Tensile Gauge TD | mil | 1.34 | 1.34 | 1.41 | 1.31 |
| Force @ Peak TD | g/in | 1674 | 1,627 | 2,075 | 1,619 |
| Strain @ Peak TD | % | 925 | 893 | 860 | 873 |
| Force @ Break TD | g/in | 1674 | 1,627 | 2,075 | 1,619 |
| Strain @ Break TD | % | 925 | 893 | 860 | 873 |
| Force @ Yield TD | g/in | 206 | 1,480 | 1,963 | 1,514 |
| Strain @ Yield TD | % | 18 | 850 | 835 | 844 |
| Force @ 5% Strain TD | g/in | 127 | 109 | 133 | 115 |
| Force @ 10% Strain TD | g/in | 175 | 157 | 179 | 162 |
| Force @ 25% Strain TD | g/in | 220 | 209 | 227 | 211 |
| Force @ 50% Strain TD | g/in | 236 | 230 | 246 | 231 |
| Force @ 100% Strain TD | g/in | 243 | 241 | 254 | 242 |
| TEA TD | FtLb/in² | 3.3 | 3.1 | 3.1 | 3 |
| Elmendorf Tear TD Arm | g | 400 | 200 | 200 | 200 |
| Elmendorf Tear TD | gf | 164 | 116 | 115 | 109 |
| 100% MD Hysteresis | | No Prestretch | No Prestretch | No Prestretch | No Prestretch |
| 1st Cycle | | | | | |
| Load @25% | g/inch | 287 | 276 | 308 | 294 |
| Load @50% | g/inch | 305 | 299 | 322 | 319 |
| Load @75% | g/inch | 318 | 309 | 330 | 328 |
| Load @100% | g/inch | 332 | 317 | 340 | 337 |
| −30 second delay | | | | | |
| Unload @100% | g/inch | 171 | 145 | 170 | 174 |
| Unload @75% | g/inch | 96 | 91 | 100 | 100 |
| Unload @50% | g/inch | 46 | 42 | 51 | 51 |
| Unload @25% | g/inch | −1 | −6 | 0 | 2 |
| −60 second delay | | | | | |
| 2nd Cycle | | | | | |
| Load @25% | g/inch | 97 | 82 | 110 | 93 |
| Load @50% | g/inch | 173 | 167 | 191 | 181 |
| Load @75% | g/inch | 230 | 226 | 249 | 242 |
| Load @100% | g/inch | 301 | 292 | 313 | 311 |
| −30 second delay | | | | | |
| Unload @100% | g/inch | 150 | 128 | 154 | 157 |
| Unload @75% | g/inch | 95 | 92 | 101 | 100 |
| Unload @50% | g/inch | 44 | 41 | 49 | 49 |

TABLE 22-continued

Physical Properties of Elastic Films Prepared from Formulations XC3-898-2407.0, XC3-888-2405.0, XC3-888-2408.0, and XC3-888-2408.1.

| Properties | Units | XC3-898-2407.0 | XC3-888-2405.0 | XC3-888-2408.0 | XC3-888-2408.1 |
|---|---|---|---|---|---|
| Unload @25% | g/inch | −1 | −6 | 1 | 2 |
| Length after Pre-stretching (started at 1") | | 1.44 | 1.44 | 1.44 | 1.44 |

| 100% MD Hysteresis | | Prestretched 4:1 | Prestretched 4:1 | Prestretched 4:1 | Prestretched 4:1 |
|---|---|---|---|---|---|
| 1st Cycle | | | | | |
| Load @25% | g/inch | 68 | 60 | 69 | 65 |
| Load @50% | g/inch | 90 | 84 | 93 | 87 |
| Load @75% | g/inch | 106 | 99 | 108 | 103 |
| Load @100% | g/inch | 125 | 115 | 121 | 121 |
| −30 second delay | | | | | |
| Unload @100% | g/inch | 56 | 48 | 48 | 47 |
| Unload @75% | g/inch | 53 | 54 | 57 | 54 |
| Unload @50% | g/inch | 34 | 36 | 38 | 36 |
| Unload @25% | g/inch | 10 | 12 | 11 | 12 |
| −60 second delay | | | | | |
| 2nd Cycle | | | | | |
| Load @25% | g/inch | 51 | 46 | 51 | 49 |
| Load @50% | g/inch | 75 | 71 | 77 | 73 |
| Load @75% | g/inch | 93 | 88 | 95 | 91 |
| Load @100% | g/inch | 118 | 109 | 114 | 114 |
| −30 second delay | | | | | |
| Unload @100% | g/inch | 35 | 33 | 32 | 32 |
| Unload @75% | g/inch | 53 | 54 | 56 | 54 |
| Unload @50% | g/inch | 34 | 36 | 37 | 36 |
| Unload @25% | g/inch | 9 | 11 | 9 | 12 |
| 50% Stretch Creep Length | Sample 5 minutes | 9.0625 | 8.875 | 8.9062 | 8.125 |
| | 1 hour | 8.8125 | 8.6875 | 8.625 | 8.625 |
| 100% Stretch Creep Length | Sample 5 minutes | 8.2812 | 7.9375 | 7.9062 | 8.3125 |
| | 1 hour | 8.0937 | 7.625 | 7.5 | 8 |

TABLE 23

Physical Properties of Elastic Films Prepared from Formulations XC3-888-2405.1, XC3-888-2405.2, XC3-888-2405.3, and XC3-888-2405.0 (High Temp.).

| Properties | Units | XC3-888-2405.1 | XC3-888-2405.2 | XC3-888-2405.3 | XC3-888-2405.0 (High Temp.) |
|---|---|---|---|---|---|
| Basis Weight | g/m$^2$ | 28 | 29 | 29 | 29 |
| Light Transmission | % | | | | |
| Tensile Gauge MD | mil | 1.36 | 1.38 | 1.37 | 1.41 |
| Force @ Peak MD | g/in | 1,862 | 1,960 | 1,595 | 1,936 |
| Strain @ Peak MD | % | 613 | 623 | 917 | 621 |
| Force @ Break MD | g/in | 1,862 | 1,960 | 1,595 | 1,936 |
| Strain @ Break MD | % | 613 | 623 | 917 | 621 |
| Force @ Yield MD | g/in | 1,634 | 1,704 | 1,415 | 1,746 |
| Strain @ Yield MD | % | 564 | 563 | 858 | 571 |
| Force @ 5% Strain MD | g/in | 147 | 169 | 134 | 173 |
| Force @ 10% Strain MD | g/in | 207 | 227 | 178 | 231 |
| Force @ 25% Strain MD | g/in | 267 | 281 | 222 | 286 |
| Force @ 50% Strain MD | g/in | 289 | 299 | 242 | 304 |
| Force @ 100% Strain MD | g/in | 305 | 314 | 255 | 319 |
| TEA MD | FtLb/in$^2$ | 2.5 | 2.7 | 3.1 | 2.6 |
| Elmendorf Tear MD Arm | g | 200 | 200 | 200 | 200 |

TABLE 23-continued

Physical Properties of Elastic Films Prepared from Formulations XC3-888-2405.1, XC3-888-2405.2, XC3-888-2405.3, and XC3-888-2405.0 (High Temp.).

| Properties | Units | XC3-888-2405.1 | XC3-888-2405.2 | XC3-888-2405.3 | XC3-888-2405.0 (High Temp.) |
|---|---|---|---|---|---|
| Elmendorf Tear MD | gf | 72 | 93 | 101 | 130 |
| Tensile Gauge TD | mil | 1.38 | 1.39 | 1.41 | 1.45 |
| Force @ Peak TD | g/in | 1,460 | 1,598 | 2,041 | 1,739 |
| Strain @ Peak TD | % | 860 | 910 | 632 | 921 |
| Force @ Break TD | g/in | 1,460 | 1,598 | 2,041 | 1,739 |
| Strain @ Break TD | % | 860 | 910 | 632 | 921 |
| Force @ Yield TD | g/in | 1,387 | 1,301 | 1,960 | 1,455 |
| Strain @ Yield TD | % | 841 | 825 | 606 | 838 |
| Force @ 5% Strain TD | g/in | 116 | 126 | 177 | 132 |
| Force @ 10% Strain TD | g/in | 159 | 172 | 237 | 180 |
| Force @ 25% Strain TD | g/in | 210 | 219 | 295 | 231 |
| Force @ 50% Strain TD | g/in | 230 | 240 | 316 | 252 |
| Force @ 100% Strain TD | g/in | 244 | 252 | 332 | 264 |
| TEA TD | FtLb/in$^2$ | 2.6 | 3 | 2.7 | 3.1 |
| Elmendorf Tear TD Arm | g | 200 | 200 | 200 | 200 |
| Elmendorf Tear TD | gf | 83 | 87 | 94 | 106 |
| 100% MD Hysteresis | | No Prestretch | No Prestretch | No Prestretch | No Prestretch |
| 1st Cycle | | | | | |
| Load @25% | g/inch | 277 | 288 | 311 | 293 |
| Load @50% | g/inch | 295 | 307 | 331 | 310 |
| Load @75% | g/inch | 302 | 313 | 337 | 317 |
| Load @100% −30 second delay | g/inch | 310 | 320 | 345 | 323 |
| Unload @100% | g/inch | 156 | 165 | 178 | 168 |
| Unload @75% | g/inch | 94 | 100 | 102 | 103 |
| Unload @50% | g/inch | 50 | 54 | 53 | 55 |
| Unload @25% −60 second delay | g/inch | 3 | 2 | 3 | 3 |
| 2nd Cycle | | | | | |
| Load @25% | g/inch | 90 | 99 | 103 | 101 |
| Load @50% | g/inch | 163 | 172 | 183 | 178 |
| Load @75% | g/inch | 215 | 225 | 241 | 233 |
| Load @100% −30 second delay | g/inch | 280 | 291 | 314 | 296 |
| Unload @100% | g/inch | 138 | 147 | 159 | 151 |
| Unload @75% | g/inch | 94 | 100 | 102 | 103 |
| Unload @50% | g/inch | 48 | 52 | 53 | 54 |
| Unload @25% | g/inch | 3 | 2 | 3 | 3 |
| Length after Pre-stretching (started at 1") | | 1.38 | 1.38 | 1.41 | 1.44 |
| 100% MD Hysteresis | | Prestretched 4:1 | Prestretched 4:1 | Prestretched 4:1 | Prestretched 4:1 |
| 1st Cycle | | | | | |
| Load @25% | g/inch | 56 | 62 | 60 | 56 |
| Load @50% | g/inch | 76 | 85 | 83 | 79 |
| Load @75% | g/inch | 89 | 100 | 99 | 94 |
| Load @100% −30 second delay | g/inch | 102 | 114 | 114 | 110 |
| Unload @100% | g/inch | 33 | 47 | 45 | 46 |
| Unload @75% | g/inch | 49 | 53 | 51 | 50 |

TABLE 23-continued

Physical Properties of Elastic Films Prepared from Formulations XC3-888-
2405.1, XC3-888-2405.2, XC3-888-2405.3, and XC3-888-2405.0 (High Temp.).

| Properties | Units | XC3-888-2405.1 | XC3-888-2405.2 | XC3-888-2405.3 | XC3-888-2405.0 (High Temp.) |
|---|---|---|---|---|---|
| Unload @50% | g/inch | 33 | 35 | 33 | 32 |
| Unload @25% | g/inch | 11 | 10 | 9 | 9 |
| −60 second delay | | | | | |
| 2nd Cycle | | | | | |
| Load @25% | g/inch | 42 | 46 | 43 | 41 |
| Load @50% | g/inch | 63 | 70 | 68 | 66 |
| Load @75% | g/inch | 77 | 86 | 85 | 82 |
| Load @100% | g/inch | 95 | 106 | 106 | 102 |
| −30 second delay | | | | | |
| Unload @100% | g/inch | 18 | 32 | 29 | 31 |
| Unload @75% | g/inch | 48 | 52 | 51 | 50 |
| Unload @50% | g/inch | 32 | 34 | 32 | 32 |
| Unload @25% | g/inch | 10 | 9 | 8 | 7 |
| 50% Stretch | 5 minutes Sample | 8.875 | 8.75 | 9 | 9 |
| Creep Length | 1 hour Sample | 8.625 | 8.6875 | 8.6562 | 8.875 |
| 100% Stretch | 5 minutes | 8.3437 | 8.1875 | 8.5312 | 8.5312 |
| Creep Length | 1 hour | 8 | 7.875 | 7.875 | 7.9062 |

Figure 9:
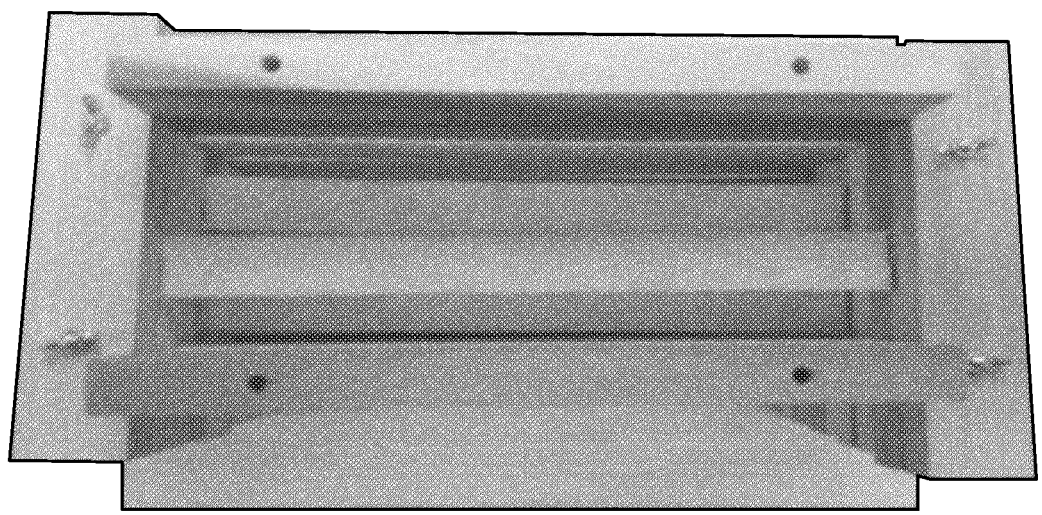
FIG. 9 is a diagrammatic view of a representative device for performing a creep test experiment.

FIG. 9 shows a representative wooden frame device configured to clamp sample films at 10.5" for use in the creep test experiments summarized in Tables 21-23 above.

To test 50% elongation, a film sample with markings spaced 7" apart is used. The measurement between markings may be determined with a ruler. The markings are stretched apart to 10.5" and the film is clamped in the wooden frame shown in FIG. 9. The samples are then placed in an oven at 100° F. (body temperature) for 24 hours. After oven exposure, the samples are removed from the frame and the distance between the marks is measured after 5 minutes and after 1 hour.

To test 100% elongation, a film sample with markings spaced 5.25" apart is used. The markings are stretched apart to 10.5" and the film is clamped in the wooden frame. The rest of the procedure is as described above for the 50% elongation test.

The invention claimed is:

1. A process for making a stretched elastic film comprising the steps of
   co-extruding at least a first composition, a second composition, and a third composition to form a molten web, the first composition forming at least one first film layer, the second composition forming at least one second film layer, and the third composition forming at least one third film layer, wherein the at least one first film layer is disposed between the at least one second film layer and the at least one third film layer, wherein the first composition comprises a polyolefin, a styrene block copolymer, a non-styrene block copolymer, or a combination thereof, and wherein the second composition and the third composition are identical or different,
   casting the molten web against a surface of a chill roll using an air knife, an air blanket, a vacuum box, or a combination thereof to form a quenched film,
   stretching the quenched film in a machine direction in at least a 2:1 draw to form a stretched film, and
   relaxing the stretched film to form the stretched elastic film,
   wherein the stretched film is not bonded to a non-woven material; and
   wherein the stretched elastic film has a load at 100% of less than about 300 grams per inch.

2. The process of claim 1, wherein the polyolefin comprises low density polyethylene, high density polyethylene, linear low density polyethylene, ultra-low density polyethylene, or a combination thereof.

3. The process of claim 1, wherein the polyolefin comprises linear low density polyethylene.

4. The process of claim 1, wherein the polyolefin comprises linear low density polyethylene and the linear low density polyethylene comprises a metallocene polyethylene.

5. The process of claim 1, wherein the polyolefin comprises polypropylene.

6. The process of claim 1, wherein the polyolefin comprises polypropylene impact copolymer.

7. The process of claim 1, wherein the styrene block copolymer comprises styrene-isoprene block copolymer, styrene-(ethylene-butylene) block copolymer, styrene-(ethylene-propylene) block copolymer, styrene-butadiene block copolymer, or a combination thereof.

8. The process of claim 1, wherein the molten web is cast against the surface of the chill roll under negative pressure by the vacuum box.

9. The process of claim 1, wherein the molten web is cast against the surface of the chill roll under positive pressure by the air knife.

10. The process of claim 1, wherein the extruding and the casting are achieved via in-line processing, and wherein the stretching is achieved via post-processing of the quenched film.

11. The process of claim 1, wherein the stretching in the machine direction is in at least a 3:1 draw.

12. The process of claim 1, wherein the stretching in the machine direction is in at least a 4:1 draw.

13. The process of claim 1, wherein at least a portion of the stretching is performed at room temperature.

14. The process of claim 1, wherein the first film layer is a core layer, and wherein each of the at least one second film layer and the at least one third film layer is an outer skin layer.

15. The process of claim 1, wherein each of the second composition and the third composition comprises a polyolefin.

16. The process of claim 1, wherein each of the second composition and the third composition comprises polyethylene, polypropylene, or a combination thereof.

17. The process of claim 1 wherein the second composition and the third composition are identical.

18. The process of claim 1, wherein the stretched elastic film, after relaxation, has a basis weight of less than or equal to about 50 gsm.

19. The process of claim 1, wherein the stretched elastic film, after relaxation, has a basis weight of less than or equal to about 30 gsm.

20. The process of claim 1, wherein the stretched elastic film, after relaxation, has a basis weight of less than or equal to about 20 gsm.

21. The process of claim 1 further comprising ageing the quenched film before the stretching to form an aged film, the aged film having an increased elasticity relative to the quenched film.

22. The process of claim 1 further comprising the step of bonding the stretched elastic film to a non-woven material, wherein the bonding step occurs after the relaxing step.

* * * * *